United States Patent
Gallego Sala et al.

(10) Patent No.: US 9,586,943 B2
(45) Date of Patent: Mar. 7, 2017

(54) BILATERALLY-SUBSTITUTED TRICYCLIC COMPOUNDS FOR THE TREATMENT OF HUMAN IMMUNODEFICIENCY VIRUS TYPE-1 (HIV-1) INFECTION AND OTHER DISEASES

(71) Applicants: CENTRO DE INVESTIGACIÓN PRINCIPE FELIPE, Valencia (ES); INSTITUTO DE SALUD CARLOS III, Madrid (ES); UNIVERSIDAD CATÓLICA DE VALENCIA "SAN VINCENTE MÁRTIR", Valencia (ES); UNIVERSITAT DE VALÈNCIA, Valencia (ES)

(72) Inventors: José Gallego Sala, Valencia (ES); Santos Fustero Lardiés, Valencia (ES); José Alcamí Pertejo, Madrid (ES); Luis González Bulnes, Valencia (ES); Ignacio Ibañez Sánchez, Valencia (ES); Silvia Catalán Muñoz, Valencia (ES); Ángel Cantero Camacho, Ciudad Real (ES); Pablo Barrio Fernández, Valencia (ES); Silvia Prado Martín, Valencia (ES)

(73) Assignees: UNIVERSITAT DE VALÈNCIA, Valencia (ES); INSTITUTO DE SALUD CARLOS III, Madrid (ES); UNIVERSIDAD CATÓLICA DE VALENCIA "SAN VINCENTE MÁRTIR", Valencia (ES)

( * ) Notice: Subject to any disclaimer, the term of this patent is extended or adjusted under 35 U.S.C. 154(b) by 0 days.

(21) Appl. No.: 14/769,298

(22) PCT Filed: Feb. 20, 2014

(86) PCT No.: PCT/EP2014/053294
§ 371 (c)(1),
(2) Date: Aug. 20, 2015

(87) PCT Pub. No.: WO2014/128198
PCT Pub. Date: Aug. 28, 2014

(65) Prior Publication Data
US 2016/0108024 A1   Apr. 21, 2016

(30) Foreign Application Priority Data

Feb. 21, 2013 (ES) .................................. 201330235

(51) Int. Cl.
*A61K 31/137* (2006.01)
*C07C 15/14* (2006.01)
(Continued)

(52) U.S. Cl.
CPC .......... *C07D 403/14* (2013.01); *A61K 31/137* (2013.01); *A61K 31/14* (2013.01);
(Continued)

(58) Field of Classification Search
CPC .............................. C07C 15/14; A61K 31/137
(Continued)

(56) References Cited

U.S. PATENT DOCUMENTS

| 3,720,690 A | 3/1973 | King et al. |
| 2006/0205728 A1 | 9/2006 | Rebek, Jr. et al. |

(Continued)

FOREIGN PATENT DOCUMENTS

| EP | 1013745 | 6/2000 |
| EP | 2308926 | 4/2011 |

(Continued)

OTHER PUBLICATIONS

Compton and Coles, "Multiple sclerosis," The Lancet, vol. 359, (Apr. 6, 2002)., pp. 1221-1231.*

(Continued)

*Primary Examiner* — Kamal Saeed
*Assistant Examiner* — Janet L Coppins
(74) *Attorney, Agent, or Firm* — Timothy H. Van Dyke; Beusse, Wolter, Sanks & Maire PLLC

(57) ABSTRACT

The invention relates to novel bilaterally-substituted tricyclic compounds and pharmaceutical compositions containing them, for use as medicaments. Due to their ability to interact with an internal RNA loop and to mimic a protein α-helix these compounds are effective in the treatment and/or prevention of HIV-1 (Human Immunodeficiency Virus-1) infection and other diseases such as those caused by other RNA viruses and by gram-positive and gram-negative bacteria, or infectious or chronic diseases responsive to (Continued)

inhibition of DNA transcription, or infectious or chronic diseases where these compounds can be used to modulate the function of RNA internal loops, or infectious or chronic diseases where these compounds can be used as agonists or inhibitors of α-helical proteins in interaction with other biomolecules.

8 Claims, 8 Drawing Sheets

(51) Int. Cl.
    *C07D 403/14*     (2006.01)
    *A61K 31/14*     (2006.01)
    *C07C 217/60*     (2006.01)
    *C07C 211/09*     (2006.01)
    *C07D 235/06*     (2006.01)
    *C07D 237/08*     (2006.01)
    *C07D 239/26*     (2006.01)
    *C07D 241/04*     (2006.01)
    *C07D 401/14*     (2006.01)

(52) U.S. Cl.
    CPC ............ *C07C 15/14* (2013.01); *C07C 211/09* (2013.01); *C07C 217/60* (2013.01); *C07D 235/06* (2013.01); *C07D 237/08* (2013.01); *C07D 239/26* (2013.01); *C07D 241/04* (2013.01); *C07D 401/14* (2013.01)

(58) Field of Classification Search
    USPC .................................. 564/306; 514/579, 634
    See application file for complete search history.

(56) References Cited

U.S. PATENT DOCUMENTS

| | | |
|---|---|---|
| 2011/0046147 A1 | 2/2011 | Hartmann et al. |
| 2011/0105545 A1 | 5/2011 | Saus et al. |

FOREIGN PATENT DOCUMENTS

| | | | |
|---|---|---|---|
| WO | 2010083501 | 7/2002 | |
| WO | 02089738 | 11/2002 | |
| WO | WO 02089738 A2 * | 11/2002 | ............ C07C 57/38 |

OTHER PUBLICATIONS

Freshney, Culture of Animal Cells: A Manual of Basic Technique, 6th Edition, 2010, pp. 1-5.*
Goodman and Gilman's, The Pharmacological Basis of Therapeutics, 12th Edition, 2011, pp. 1 and 595-597.*
Huff, J. Med. Chem., 1991, pp. 2305-2314.*
Hang Yin et al., JACS, 2005, 127(29), 10191-10196.
Laura Anderson et al., J. Org. Chem., 2010, 75(12), 4288-4291.
Kutzki, O et al., JACS, 2002, 124(40), 11838-11839.
Jason R. Thomas et al., Chemical Reviews, 2008, 108(4), 1171-1224.
Kiao, G et al., Bioorganic & Medicinal Chemistry, 2001, 9, 1097-1113.
Hang Yin et al., Angewandte Chemie, 2005,44(18), 2704-2707.
Ghosh Usha et al., Bioorganic & Medicinal Chemistry, 2003, 11(4), 629-657.
Weisi Wang et al., Medicinal Research Reviews, 2012, 32(6), 1159-1196.
Jessica M. Davis et al., Organic Letters, 2005, 7(24), 5405-5408.
Henry J. Shine et al., J. Org. Chem., 1990, 55(13), 4086-4089.
Chalk, A J Ed, Tetrahedron, 1974,30(11), 1387-1391.
Usha Ghosh et al., J. Heterocyclic Chemistry, 2002, 39(5), 1101-1104.
Satoshi Horikoshi et al., Organic Process Research & Development, 2008, 12(2), 257-263.
Daniel A. Scola et al., J. Org. Chem., 1965, 30(2), 384-388.
K-W Glombitza et al., Planta Medica, 1977, 32(5), 33-45.
Gregory Burzicki et al., Synthesis, 2010, 16, 2804-2810.
Burmistrov and Makarevich, J. Org. Chem. of the USSR., 1975, 11, 874-877.
Luis González-Bulnes, et al., Angewandte Chemie, 2013, 52(50), 13405-13409.
Clouser, C.L. et al., Biological & Medicinal Chemistry Letters, 2012, 22, 6642-6646.
Stevens, C.B. et al., Bioorganic & Medicinal Chemistry Letters, 2013, 23, 1703-1706.
Tsygankova, I.G. & Ahenodarova S.M., Russian J. of General Chemistry, 2011, 81(5), 913-919.
Ortega, A. et al., Bioorganic & Medicinal Chemistry Letters, 2011, 21, 2183-2187.
Singh, S.B. et al., J. of Industrial Microbiology & Biotechnology, 2003, 30, 721-731.
Gallego, J. et al., Acc. Chem. Res., 2001, 34, 836-843.
Battiste, J.L. et al., Science, 1996, 273, 1547-1551.
Tan, R. et al., Cell, 1993, 73, 1031-1040.
Daugherty, M.D. et al., Nat. Struct. Mol. Biol., 2010, 17(11): 1337-1342.
Lirui Guan et al., ACS Chem. Biol., 2012, 7, 73-86.
Hermann, et al., Current Opinion in Structural Biology 2005, 15, 355-366.
Luedtke, N.W. et al., Biochemistry, 2003, 42(39), 11391-11403.
Lacourciere, K.A. et al., Biochemistry 2000, 39, 5630-5641.
Groom, H.C.T. et al., Journal of General Virology (2009), 90, 1303-1318.
Richman, D.D. et al., Science, 2009, 323,1304-1307.
Ernst, J.T. et al., Angew. Chem. Int. Ed. 2002,41(2), 278-281.

* cited by examiner (a)

(b)

RRE:IIS-420, 1:0, 1:1, 1:2

RRE:IIS-806, 1:0, 1:1, 1:2

RRE:JB-398 1:0, 1:1, 1:2, 1:6

SEQUENCE LISTING

<160> NUMBER OF SEQ ID NOS: 5

<210> SEQ ID NO 1
<211> LENGTH: 28
<212> TYPE: RNA

```
<213> ORGANISM: Artificial Sequence
<220> FEATURE:
<223> OTHER INFORMATION: RRE Hairpin

<400> SEQUENCE: 1
gcugggcgca cuucggugac gguacagc                                        28

<210> SEQ ID NO 2
<211> LENGTH: 26
<212> TYPE: RNA
<213> ORGANISM: Artificial Sequence
<220> FEATURE:
<223> OTHER INFORMATION: Control RRE

<400> SEQUENCE: 2
gcugggcgga cuucggugcg cccagc                                          26

<210> SEQ ID NO 3
<211> LENGTH: 27
<212> TYPE: RNA
<213> ORGANISM: Artificial Sequence
<220> FEATURE:
<223> OTHER INFORMATION: TAR Hairpin

<400> SEQUENCE: 3
gcugaucuga cacuucggug ucucagc                                         27

<210> SEQ ID NO 4
<211> LENGTH: 22
<212> TYPE: PRT
<213> ORGANISM: Artificial Sequence
<220> FEATURE:
<223> OTHER INFORMATION: REV Peptide

<400> SEQUENCE: 4

Thr Arg Gln Ala Arg Arg Asn Arg Arg Arg Arg Trp Arg Glu Arg Gln
1               5                   10                  15

Arg Ala Ala Ala Ala Arg
            20

<210> SEQ ID NO 5
<211> LENGTH: 27
<212> TYPE: PRT
<213> ORGANISM: Artificial Sequence
<220> FEATURE:
<223> OTHER INFORMATION: FITC Labeled Peptide

<400> SEQUENCE: 5

Phe Ile Thr Cys Gly Thr Arg Gln Ala Arg Arg Asn Arg Arg Arg Arg
1               5                   10                  15

Trp Arg Glu Arg Gln Arg Ala Ala Ala Ala Arg
            20                  25
```

BILATERALLY-SUBSTITUTED TRICYCLIC COMPOUNDS FOR THE TREATMENT OF HUMAN IMMUNODEFICIENCY VIRUS TYPE-1 (HIV-1) INFECTION AND OTHER DISEASES

FIELD OF THE INVENTION

The invention relates to novel bilaterally-substituted tricyclic compounds and pharmaceutical compositions containing them, for use as medicaments.

Due to their ability to interact with an internal RNA loop and to mimic a protein α-helix these compounds are effective in the treatment and/or prevention of HIV-1 (Human Immunodeficiency Virus-1) infection and other diseases such as those caused by other RNA viruses and by gram-positive and gram-negative bacteria, or infectious or chronic diseases responsive to inhibition of DNA transcription, or infectious or chronic diseases where these compounds can be used to modulate the function of RNA internal loops, or infectious or chronic diseases where these compounds can be used as agonists or inhibitors of α-helical proteins in interaction with other biomolecules.

BACKGROUND OF THE INVENTION

According to the 2011 report of the World Health Organisation (WHO), infections caused by HIV-1 affected 34 million people worldwide in 2010, causing 2.7 million new cases and 1.8 million deaths.

In recent years, the use of antiretroviral therapy has resulted in a reduction of AIDS incidence and mortality. The current treatment of HIV-1 infection is based on combinations of three or four drugs that either inhibit the protease, reverse transcriptase or integrase of the virus, or block viral entry into the cell. However, these treatments do not eliminate the infection(1, 2). The appearance of resistance and the lack of an effective vaccine further underscore the need to search for new drugs aimed towards alternative targets. There is therefore an urgent need for new treatments effective at eliminating the infection caused by HIV-1.

RNA plays a central role in the functioning of living organisms(3), and many human, bacterial and viral RNA molecules have considerable therapeutic potential. Two strategies are currently being used to target these molecules. The first approach is based on the generation of antisense or RNAi molecules, aimed to base-pair with the intended RNA and in this way promote its degradation or block translation. The second strategy consists in the synthesis of small organic molecules designed to specifically recognize the cavities formed by tertiary RNA structures and interfere with their function(4, 5).

Functional and structured RNA motifs are not easily targeted by antisense agents and have the advantage of their high sequence and/or three-dimensional structure conservation. In the anti-infective field this is important, as it could result in a slower emergence of resistance to agents acting on them. Numerous natural products with antibiotic activity exert their action by binding to sites within bacterial ribosomal RNA. However, the development of new RNA-binding anti-infective agents has been hampered by the difficulties posed by these structures, which have limited physicochemical diversity and are often flexible(4-6). In order for this approach to be successful, it is essential to identify novel chemical scaffolds as well as new mechanisms of specific recognition of RNA structure.

The Rev Recognition Element (RRE) is a strongly conserved 350-nucleotide structure located in the env gene of human immunodeficiency virus type-1 (HIV-1) RNA. Within subdomain IIB of the RRE, the unusually widened major groove of a large GGCG:ACGGUA internal loop forms a high-affinity complex(7) with the arginine-rich α-helix of Rev (FIG. 1a), a virally-encoded 116-amino acid protein adopting a helix-turn-helix conformation(8, 9). This initial interaction between internal loop IIB of the RRE and the RNA-binding α-helix of Rev (hereafter designated $Rev_{34-50}$) is essential for virus viability, as it triggers a cascade of events allowing the transport of unspliced or incompletely spliced viral RNA molecules to the cytoplasm of the infected cell in the late phase of the virus cycle. These events include the incorporation of additional Rev molecules to the complex(10), and the tethering of this RRE-Rev ribonucleoprotein to the Crm1 host export factor.

Evidence accumulated in recent years indicates that Rev has pleiotropic effects(11) in addition to RNA nuclear export, this protein has been shown to enhance translation and packaging(11, 12) and to control de nucleocytoplasmic shuttling of the HIV-1 integrase(13). Clearly, Rev represents a pivotal target for HIV-1 therapy. However, up to now the rational design of Rev-based inhibitors has remained an elusive goal, and none of the Rev- or RRE-based inhibitors evaluated so far have entered clinical use(14).

SUMMARY OF THE INVENTION

The present invention relates to novel compounds of general Formula I and their pharmaceutically acceptable salts, esters, solvates, isomers and prodrugs, and their use as medicaments, in particular for the prevention and/or treatment of HIV-1 infection and other diseases. Other diseases include, but are not limited to, diseases caused by other RNA viruses and by gram-positive and gram-negative bacteria, as well as infectious or chronic diseases responsive to the inhibition of DNA transcription, and infectious or chronic diseases where these compounds may be used to modulate the function of RNA internal loops, or as agonists or inhibitors of α-helical proteins in interaction with other biomolecules.

In another aspect the invention relates to pharmaceutical compositions containing the compounds of the invention and their use as medicaments.

The present invention is based on the in silico design, organic synthesis and biological evaluation of bilaterally-substituted 1,4-linked tricyclic compounds of formula I. The introduction of ortho substituents on both sides of a tricyclic scaffold ensures a 360° side-chain projection similar to that observed in the high-affinity RRE IIB-$Rev_{34-50}$ complex, where two thirds of the α-helix are surrounded by RNA. This conformation, together with their chemical composition, allows the compounds to interact in a specific manner with the RRE internal loop IIB of HIV-1 RNA. Experiments confirmed that the compounds of the invention bound to internal loop IIB of the RRE by mimicking the RNA-binding α-helix of the HIV-1 protein Rev, and were capable of inhibiting the RRE-Rev interaction both in vitro and ex vivo. In addition, the most potent inhibitors blocked HIV-1 replication ex vivo and exerted this effect in post-integration steps of the virus life cycle, as expected. In addition to their action on the RRE-Rev system, a cellular assay showed that bilaterally-substituted p-terphenyls inhibited transcription mediated by the HIV-1 LTR promoter. No cellular toxicity was detected in ex vivo assays.

The compounds of the invention act on the viral RRE-Rev system, a therapeutic target that is essential for HIV-1 replication and has not been exploited yet. They have a novel, non-peptidic, synthetic scaffold able to recognise a strongly conserved viral RNA motif. This can result in a slower appearance of resistance relative to the compounds currently used in the clinic, which act on less conserved protein targets of the virus. Moreover, since both RRE and Rev are coded by the virus and no cellular factor is involved in the RRE-Rev interaction, the RRE-Rev inhibitors of the invention may block HIV-1 replication with lower effects on cellular components and therefore less toxicity.

Furthermore, experiments based on disk susceptibilities indicated that the compounds of the invention had antibiotic activity against gram-positive and gram-negative bacteria.

Compounds of the present invention are represented by the following Formula I:

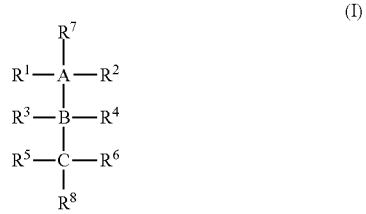

wherein:

A, B and C are independently a six-membered ring selected from benzene, pyridine, pyrazine, pyrimidine, pyridazine, cyclohexane, oxane, piperidine and piperazine The rings A, B and C are attached to each other in para positions with single bonds $R^1$, $R^2$, $R^3$, $R^4$, $R^5$ and $R^6$ are in ortho or meta positions in relation to the atoms of attachment of the six-membered rings $R^7$ and $R^8$ are in para positions in relation the atoms of attachment of the six-membered rings $R^1$ and $R^2$ are in bilateral position with respect to each other (1,3 or 1,4 disubstituted in relation to each other) in the six-membered ring and are independently selected from hydrogen, halogen, hydroxyl, alkoxy, alkylamine, alkylguanidine, alkylamide, alkyl ester, alkyl carboxylate, hydroxyalkyl, alkoxyalkyl, haloalkyl and alkyl. $R^1$ and $R^2$ may also be independently selected from alkyl thioether and alkyl thioester $R^3$ and $R^4$ are in bilateral position with respect to each other (1,3 or 1,4 disubstituted in relation to each other) in the six-membered ring and are independently selected from hydrogen, halogen, hydroxyl, alkoxy, alkylamine, alkylguanidine, alkylamide, alkyl ester, alkyl carboxylate, hydroxyalkyl, alkoxyalkyl, haloalkyl and alkyl. $R^3$ and $R^4$ may also be independently selected from alkyl thioester, alkyl thioester, aryl, aryloxy, aryl ester, aryl amide, aryl alkyl, aryl alkoxy, aryl alkyl ester and aryl alkyl amide $R^5$ and $R^6$ are in bilateral position with respect to each other (1,3 or 1,4 disubstituted in relation to each other) in the six-membered ring and are independently selected from hydrogen, halogen, hydroxyl, alkoxy, alkylamine, alkylguanidine, alkylamide, alkyl ester, alkyl carboxylate, hydroxyalkyl, alkoxyalkyl, haloalkyl and alkyl. $R^5$ and $R^6$ may also be independently selected from alkyl thioether and alkyl thioester $R^7$ and $R^8$ are independently selected from hydrogen, halogen, hydroxyl, alkoxy, alkylamine, alkylguanidine, alkylamide, alkyl ester, alkyl carboxylate, hydroxyalkyl, alkoxyalkyl, haloalkyl, alkyl, aryl alkoxy and aryl ester

DETAILED DESCRIPTION OF THE INVENTION

Figure 1:
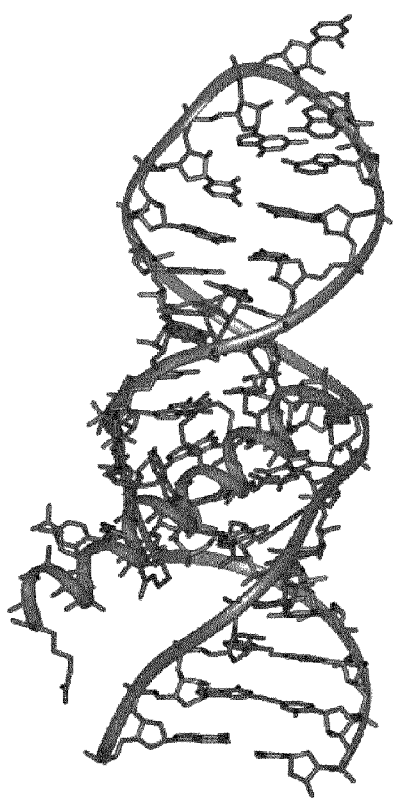
FIG. 1 represents (a) the three-dimensional structure of the complex formed by internal loop IIB of the RRE and the RNA-binding α-helix of the Rev protein, $Rev_{34-50}$(7), and (b) a schematic representation of a bilaterally-substituted p-terphenyl molecule superposed on an α-helix.
Figure 1:
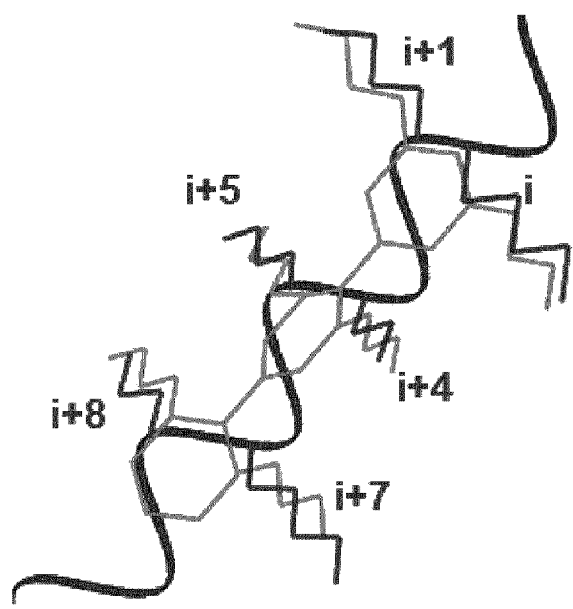

In one aspect of the present invention, there is provided a compound represented by the following Formula I:

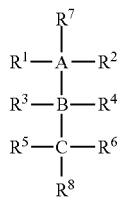

(I)

wherein:

A, B and C are independently a six-membered ring selected from benzene, pyridine, pyrazine, pyrimidine, pyridazine, cyclohexane, oxane, piperidine and piperazine The rings A, B and C are attached to each other in para positions with single bonds $R^1$, $R^2$, $R^3$, $R^4$, $R^5$ and $R^6$ are in ortho or meta positions in relation to the atoms of attachment of the six-membered rings $R^7$ and $R^8$ are in para positions in relation the atoms of attachment of the six-membered rings $R^1$ and $R^2$ are in bilateral position with respect to each other (1,3 or 1,4 disubstituted in relation to each other) in the six-membered ring and are independently selected from hydrogen, halogen, hydroxyl, alkoxy, alkylamine, alkylguanidine, alkylamide, alkyl ester, alkyl carboxylate, hydroxyalkyl, alkoxyalkyl, haloalkyl and alkyl. $R^1$ and $R^2$ may also be independently selected from alkyl thioether and alkyl thioester $R^3$ and $R^4$ are in bilateral position with respect to each other (1,3 or 1,4 disubstituted in relation to each other) in the six-membered ring and are independently selected from hydrogen, halogen, hydroxyl, alkoxy, alkylamine, alkylguanidine, alkylamide, alkyl ester, alkyl carboxylate, hydroxyalkyl, alkoxyalkyl, haloalkyl and alkyl. $R^3$ and $R^4$ may also be independently selected from alkyl thioether, alkyl thioester, aryl, aryloxy, aryl ester, aryl amide, aryl alkyl, aryl alkoxy, aryl alkyl ester and aryl alkyl amide $R^5$ and $R^6$ are in bilateral position with respect to each other (1,3 or 1,4 disubstituted in relation to each other) in the six-membered ring and are independently selected from hydrogen, halogen, hydroxyl, alkoxy, alkylamine, alkylguanidine, alkylamide, alkyl ester, alkyl carboxylate, hydroxyalkyl, alkoxyalkyl, haloalkyl and alkyl. $R^5$ and $R^6$ may also be independently selected from alkyl thioether and alkyl thioester $R^7$ and $R^8$ are independently selected from hydrogen, halogen, hydroxyl, alkoxy, alkylamine, alkylguanidine, alkylamide, alkyl ester, alkyl carboxylate, hydroxyalkyl, alkoxyalkyl, haloalkyl, alkyl, aryl alkoxy and aryl ester and salts, esters, isomers, solvates, hydrates or prodrugs thereof.

The term "alkyl" as used herein refers to a hydrocarbon moiety having from 1 to 12 carbon atoms. It can be cyclic or acyclic, saturated or unsaturated, branched or linear, such as methyl, ethyl, propyl, isopropyl, butyl, t-butyl, hexyl, propenyl, cyclopropyl, cyclopentyl, cyclohexyl and the like.

The term "alkoxy" refers to an alkyl moiety as defined herein, attached to an oxygen atom. It includes for example methoxy, ethoxy, cyclohexylmethoxy, morpholinemethoxy and the like.

The term "aryl" refers to aromatic ring systems having 5 to about 50 atoms, with from about 6 to about 14 atoms or about 5 to 6 atoms wherein the atoms can be independently selected from C, N, O or S. The aryl group can be used alone or as part of another group. The aryl group can have a single ring or multiple rings, condensed or joined by single bonds. Examples include but are not limited to phenyl, naphthyl, biphenyl, anthryl, indanyl, trifluoromethylbenzyl, pyridyl, pyrimidyl, benzimidazole, terphenyl, benzoxazole, benzothiazole, indazole, quinazoline, thiophenyl and the like.

Some preferred compounds of formula (I) are those wherein $R^1$, $R^2$, $R^5$ and $R^6$ are not hydrogen. Compounds wherein at least one of $R^3$ or $R^4$ is not hydrogen or where none of $R^1$, $R^2$, $R^3$, $R^4$, $R^5$ and $R^6$ are hydrogen are particularly preferred.

Preferred compounds of the invention include compounds of formula (I) wherein $R^3$ and $R^4$ are independently selected from hydrogen, halogen, hydroxyl, alkoxy, alkylamine, alkylguanidine, alkylamide, alkyl ester, alkyl carboxylate, hydroxyalkyl, alkoxyalkyl, haloalkyl and alkyl but compounds wherein $R^3$ and $R^4$ are independently selected from aryl, aryloxy, alryl ester, aryl amide, aryl alkyl, aryl alcoxy, aryl akyl ester and aryl alkyl amide are also preferred.

Some preferred compounds of formula (I) include those wherein one or both $R^1$ and $R^2$ are independently selected from alkyl thioether and alkyl thioester. Also preferred are compounds wherein one or both $R^3$ and $R^4$ are independently selected from alkyl thioether and alkyl thioester. Compounds where one or both $R^5$ and $R^6$ are independently selected from alkyl thioether and alkyl thioester may also be preferred.

Particularly preferred compounds of formula I include those wherein $R^1$ and $R^2$ are 1,3 disubstituted in relation to each other in the six-membered ring, $R^3$ and $R^4$ are 1,3 disubstituted in relation to each other in the six-membered ring, and $R^5$ and $R^6$ are 1,3 disubstituted in relation to each other in the six-membered ring Compounds of the invention having $R^7$ and $R^8$ different from hydrogen are also preferred. In this case, compounds having substituents different from hydrogen in $R^1$, $R^2$, $R^5$ and $R^6$ are of particular interest. Particularly preferred are compounds wherein $R^1$, $R^2$, $R^5$, $R^6$, $R^7$ and $R^8$ are not hydrogen and one of $R^3$ and $R^4$ is not hydrogen. Compounds where all substituents are not hydrogen are preferred.

A, B and C can be benzene, pyridine, pyrazine, pyrimidine, pyridazine, cyclohexane, oxane, piperidine and piperazine. Some preferred compounds have at least one benzene ring. Particularly preferred compounds have two benzene rings. Some preferred compounds have three benzene rings. Also preferred are compounds where two of the rings are benzene and the third ring is pyrimidine, pyridine, pyridazine or piperazine. Preferred compounds are also those wherein A and C are benzene and B is pyrimidine, pyridine, pyridazine or piperazine. In some preferred compounds A, B and C are pyridine. Compounds wherein A, B and C are piperazine are also preferred. Compounds wherein A, B and C are cyclohexane are also compounds of interest, in particular compounds where all substituents $R^1$ to $R^8$ are not hydrogen. Compounds wherein A, B and C are pyrimidine are also preferred. In some compounds of interest, when rings A and/or B and/or C are piperazine, the ring nitrogen atoms occupy the positions of attachment of the six-membered rings. When ring B is pyridazine, preferred compounds include those wherein the N atoms occupy ortho or meta positions in relation to the atoms of B attached to A and C. When rings A and/or B and/or C are pyridine or pyrimidine, some preferred compounds are those wherein the ring nitrogen atoms are in ortho or meta positions in relation to the atoms of attachment of the six-membered rings, Compounds where ring A is pyridine or pyridimine and the N atoms occupy ortho positions in relation to the atom of A attached to B may be particularly preferred. When ring B is pyridine or pyrimidine, compounds where the N atoms occupy ortho positions in relation to the atom of B attached to C may be preferred. When ring C is pyridine or pyrimidine, compounds where the N atoms occupy meta positions in relation to the atom of C attached to B may be preferred.

For example, preferred compounds of formula (I) can include compounds shown below:

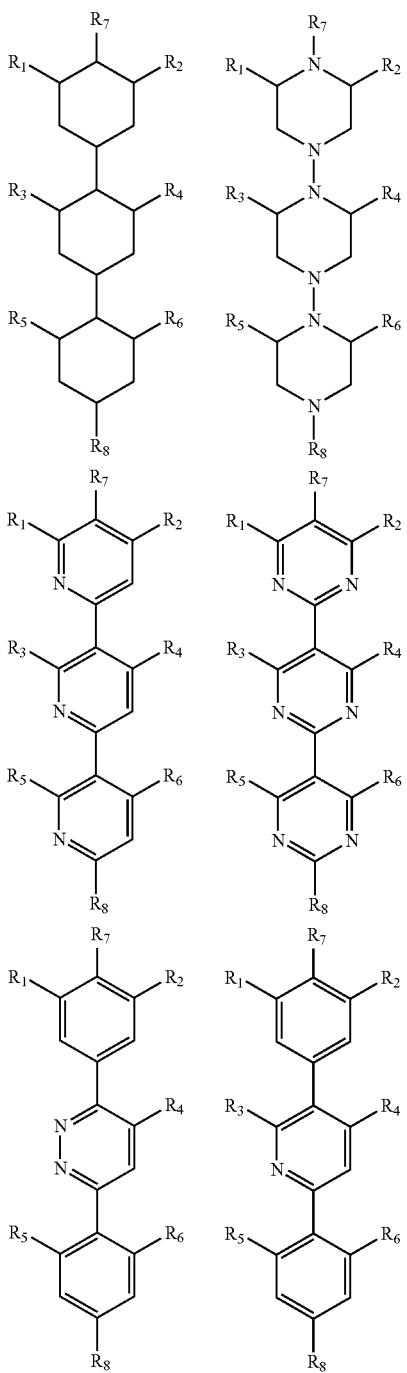

-continued

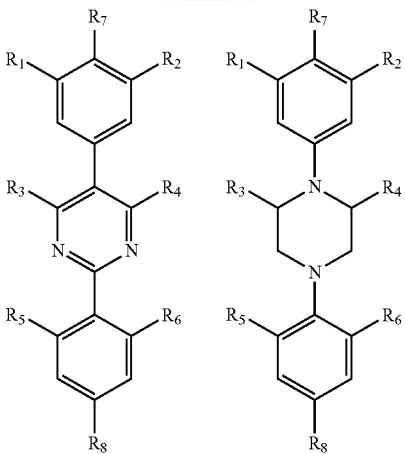

Any compounds of formula (I) resulting from all possible combinations of the preferred definitions of A, B, C, $R^1$, $R^2$, $R^3$, $R^4$, $R^5$, $R^6$, $R^7$ and $R^8$ described above also form part of the invention.

Preferred compounds of the invention also include compounds of formula (I) wherein:

A, B and C are benzene, $R^1$ and $R^2$ are in bilateral 1,3 disubstitution relative to each other in benzene A and meta in relation to the carbon atom of A attached to benzene B; and are independently selected from optionally substituted aminomethyl, aminoethyl and aminopropyl $R^3$ and $R^4$ are in bilateral 1,3 disubstitution relative to each other in benzene B and ortho in relation to the carbon atom of B attached to benzene A; and are independently selected from, hydrogen, halogen, hydroxyl, (C1-C6) alkoxy, (C1-C6) optionally substituted alkylamide, (C1-C6) optionally substituted alkyl ester, (C1-C6) hydroxyalkyl, (C1-C6) haloalkyl, (C1-C6) alkoxyalkyl and (C1-C8) alkyl. $R^3$ and $R^4$ may also be independently selected from (C1-C6) alkyl thioether, (C1-C6) alkyl thioester, aryl, aryloxy, aryl ester, aryl amide, aryl (C1-C8) alkyl, aryl (C1-C6) alkoxy, aryl (C1-C6) alkyl ester and aryl (C1-C6) alkyl amide.

$R^5$ y $R^6$ are in bilateral 1,3 disubstitution relative to each other in benzene C and ortho in relation to the carbon atom of C attached to benzene B; and are independently selected from optionally substituted aminomethyl, aminoethyl and aminopropyl $R^7$ y $R^8$ are independently selected from hydrogen, halogen, hydroxyl, (C1-C10) alkoxy, (C1-C10) alkylamine, (C1-C10) alkylguanidine, (C1-C10) alkylamide, (C1-C10) alkylester, (C1-C10) hydroxyalkyl, (C1-C10) alkoxyalkyl, (C1-C10) haloalkyl, (C1-C10) alkyl, aryl alkoxy and aryl ester.

Examples of compounds represented by general formula I are as follows:
JB-399
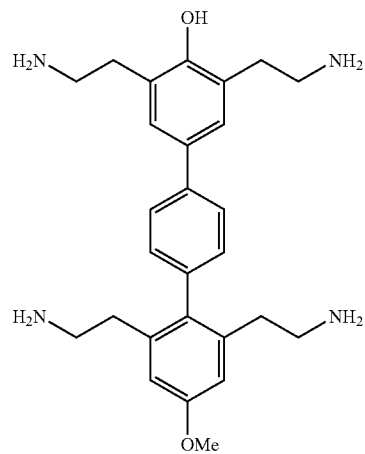
IIS-358
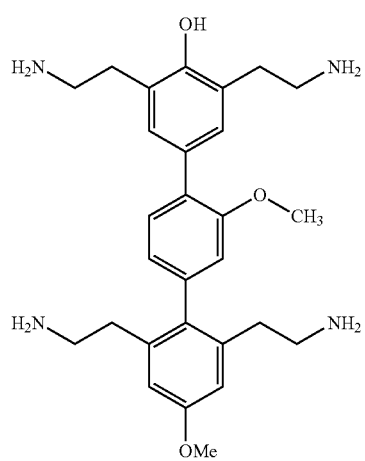
IIS-311
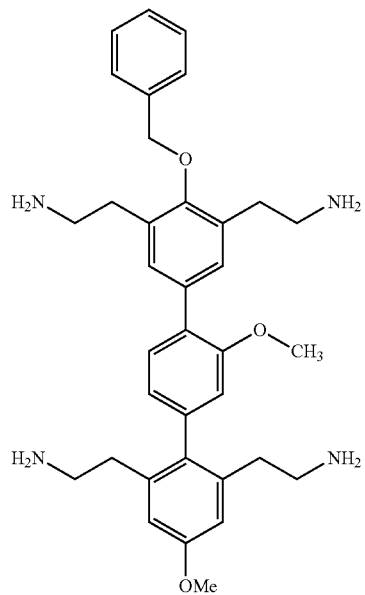
IIS-530
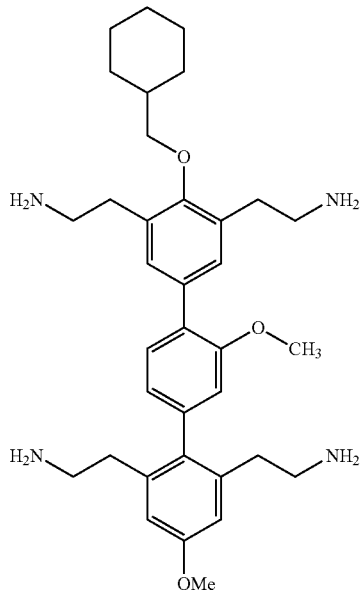
IIS-478
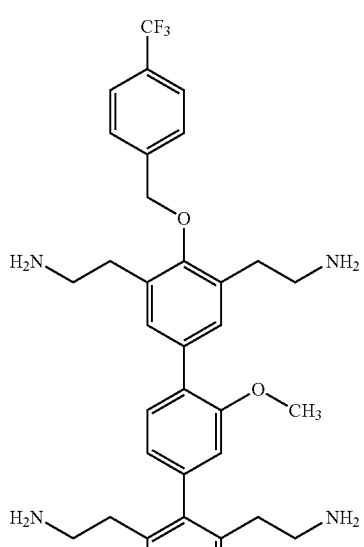
IIS-792
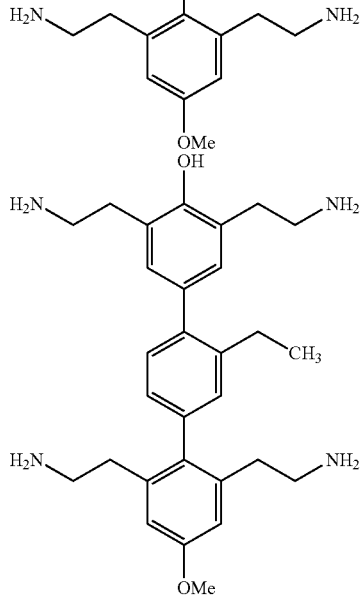

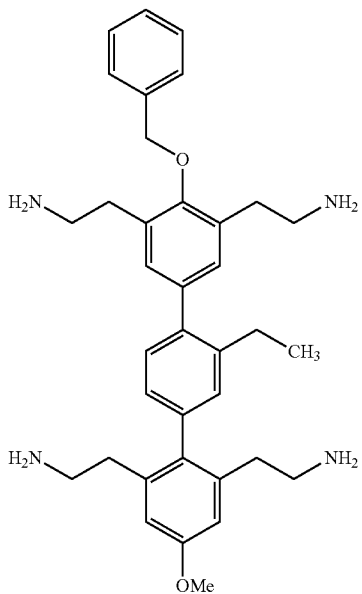

IIS-758

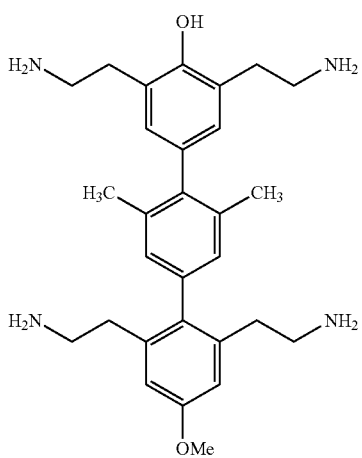

IIS-420

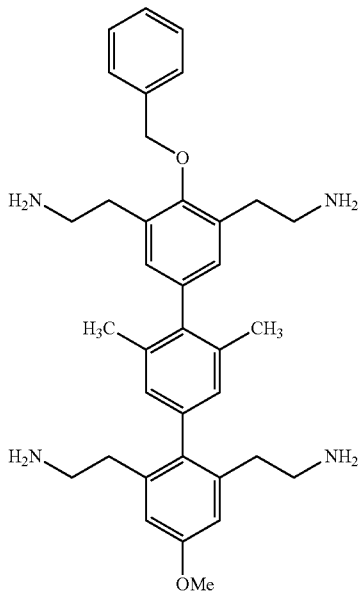

IIS-375

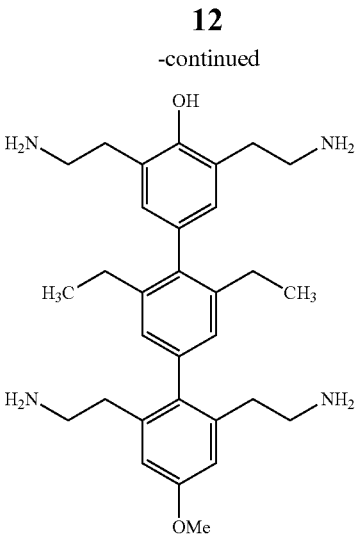

IIS-806

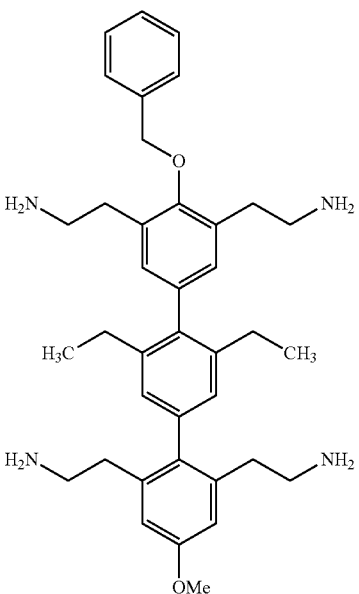

IIS-771

Particularly preferred compounds include:
JB-399: 2",3,5,6"-tetrakis(2-aminoethyl)-4"-methoxy-[1,1':4',1"-terphenyl]-4-ol
IIS-358: 2",3,5,6"-tetrakis(2-aminoethyl)-2',4"-dimethoxy-[1,1':4',1"-terphenyl]-4-ol
IIS-311: 2,2',2",2'''-(4"-(benzyloxy)-3',4-dimethoxy-[1,1':4',1"-terphenyl]-2,3",5",6-tetrayl)tetraethanamine
IIS-478: 2,2',2",2'''-(3',4-dimethoxy-4"-((4-(trifluoromethyl)benzyl)oxy)-[1,1':4',1"-terphenyl]-2,3",5",6-tetrayl)tetraethanamine
IIS-530: 2,2',2",2'''-(4"-(cyclohexylmethoxy)-3',4-dimethoxy-[1,1':4',1"-terphenyl]-2,3",5",6-tetrayl)tetraethanamine
IIS-420: 2",3,5,6"-tetrakis(2-aminoethyl)-4"-methoxy-2',6'-dimethyl-[1,1':4',1"-terphenyl]-4-ol
IIS-375: 2,2',2",2'''-(4"-(benzyloxy)-4-methoxy-3',5'-dimethyl-[1,1':4',1"-terphenyl]-2,3",5",6-tetrayl)tetraethanamine
IIS-792: 2",3,5,6"-tetrakis(2-aminoethyl)-2'-ethyl-4"-methoxy-[1,1':4',1"-terphenyl]-4-ol
IIS-758: 2,2',2",2'''-(4"-(benzyloxy)-3'-ethyl-4-methoxy-[1,1':4',1"-terphenyl]-2,3",5",6-tetrayl)tetraethanamine
IIS-806: 2",3,5,6"-tetrakis(2-aminoethyl)-2',6'-diethyl-4"-methoxy-[1,1':4',1"-terphenyl]-4-ol IIS-711: 2,2',2'',2'''-(4''-(benzyloxy)-3',5'-diethyl-4-methoxy-[1,1':4',1''-terphenyl]-2,3'',5'',6-tetrayl)tetraethanamine Most preferred compounds include:

IIS-806: 2'',3,5,6''-tetrakis(2-aminoethyl)-2',6'-diethyl-4''-methoxy-[1,1':4',1''-terphenyl]-4-ol IIS-711: 2,2',2'',2'''-(4''-(benzyloxy)-3',5'-diethyl-4-methoxy-[1,1':4',1''-terphenyl]-2,3'',5'',6-tetrayl)tetraethanamine IIS-420: 2'',3,5,6''-tetrakis(2-aminoethyl)-4''-methoxy-2',6'-dimethyl-[1,1':4',1''-terphenyl]-4-ol IIS-375: 2,2',2'',2'''-(4''-(benzyloxy)-4-methoxy-3',5'-dimethyl-[1,1':4',1''-terphenyl]-2,3'',5'',6-tetrayl)tetraethanamine Further examples of compounds of formula (I) are:

2,6-bis(2-aminoethyl)-4-(6-(2,6-bis(2-aminoethyl)-4-methoxyphenyl)-4-methylpyridazin-3-yl)phenol

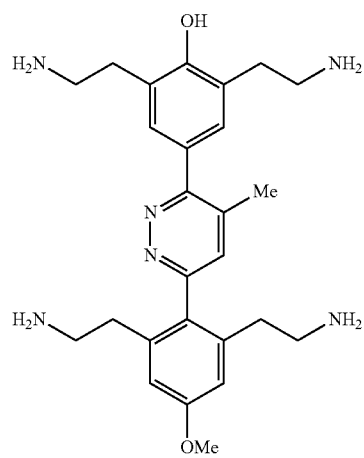 [SMILES: COc1cc(CCN)c(-c2cc(C)c(-c3cc(CCN)c(O)c(CCN)c3)nn2)c(CCN)c1]

2,6-bis(2-aminoethyl)-4-(2-(2,6-bis(2-aminoethyl)-4-methoxyphenyl)-4,6-diethylpyrimidin-5-yl)phenol

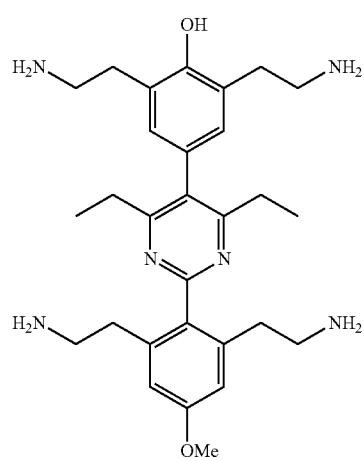 [SMILES: CCc1nc(-c2c(CCN)cc(OC)cc2CCN)nc(CC)c1-c1cc(CCN)c(O)c(CCN)c1]

2'-(2-(1H-benzo[d]imidazol-2-yl)ethyl)-2'',3,5,6''-tetrakis(2-aminoethyl)-4''-methoxy-6'-methyl-[1,1':4',1''-terphenyl]-4-ol

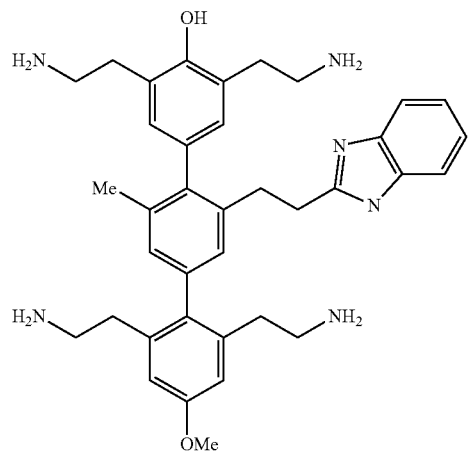 [SMILES: COc1cc(CCN)c(-c2cc(C)c(-c3cc(CCN)c(O)c(CCN)c3)c(CCc3nc4ccccc4[nH]3)c2)c(CCN)c1]

2,3'',5'',6-tetrakis(2-aminoethyl)-3',5'-bis(fluoromethyl)-[1,1':4',1''-terphenyl]-4,4''-diol

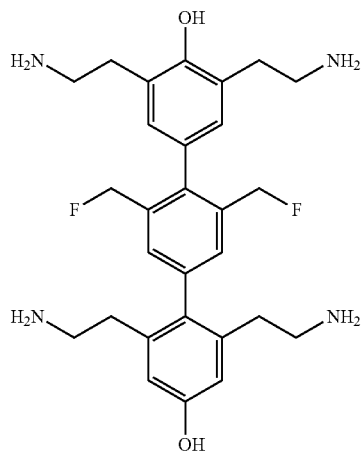 [SMILES: NCCc1cc(-c2c(CF)cc(-c3c(CCN)cc(O)cc3CCN)cc2CF)cc(CCN)c1O]

2,2'',5,5''-tetrakis(2-aminoethyl)-2',5'-dimethyl-[1,1':4',1''-terphenyl]-4,4''-diol

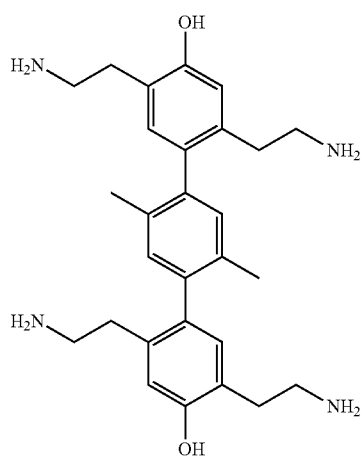 [SMILES: Cc1cc(-c2cc(CCN)c(O)cc2CCN)c(C)cc1-c1cc(CCN)c(O)cc1CCN]

2,3",5",6-tetrakis(3-aminopropyl)-2',5'-dimethyl-[1,1':4',1"-terphenyl]-4,4"-diol

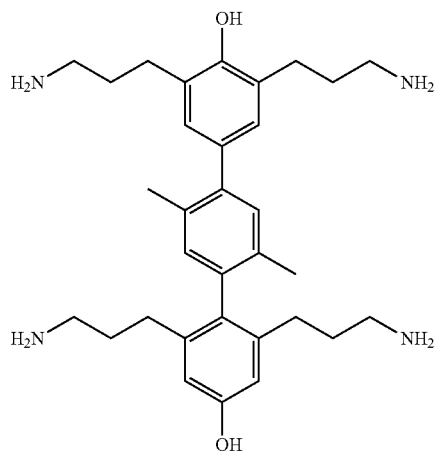 [SMILES: Cc1cc(-c2c(CCCN)cc(O)cc2CCCN)c(C)cc1-c1cc(CCCN)c(O)c(CCCN)c1]

2,2',2",2'''-(2',4'-bis(fluoromethyl)-[2,3':6',3"-terpyridine]-2",4,4",6-tetrayl)tetrakis(ethan-1-amine)

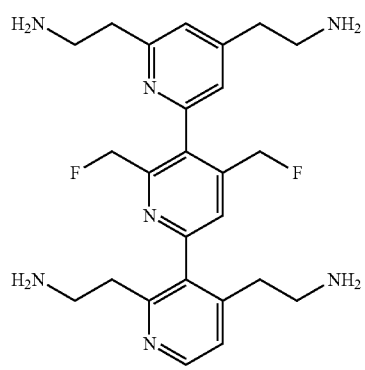 [SMILES: NCCc1cc(CCN)nc(-c2c(CF)cc(-c3c(CCN)ccnc3CCN)nc2CF)c1]

3,3',3",3'''-(4"-(benzyloxy)-4-methoxy-3',5'-dimethyl-[1,1':4',1"-terphenyl]-2,3",5",6-tetrayl)tetrapropanoate

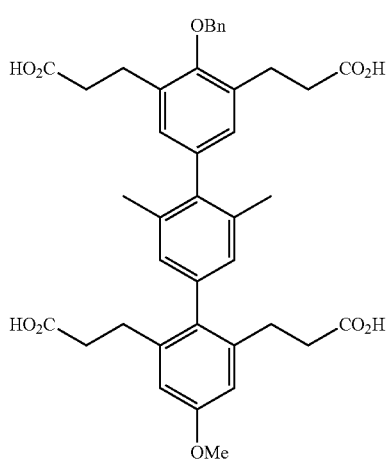 [SMILES: COc1cc(CCC(=O)O)c(-c2cc(C)c(-c3cc(CCC(=O)O)c(OCc4ccccc4)c(CCC(=O)O)c3)c(C)c2)c(CCC(=O)O)c1]

2,2'-(2-(benzyloxy)-5-(4-(2,6-bis(2-aminoethyl)-4-methoxyphenyl)-2,6-diethylpiperazin-1-yl)-1,3-phenylene)diethanamine

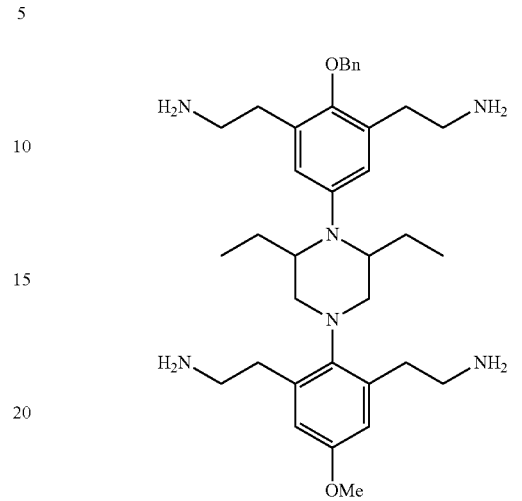

2,2',2",2'''-(4',6'-dimethyl-[2,5':2',5"-terpyrimidine]-4,4",6,6"-tetrayl)tetraethanamine

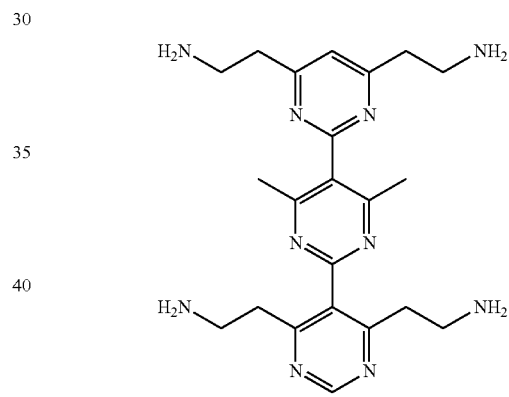

In an additional aspect of the invention, a compound of formula (I) is useful for the treatment and/or prevention of a disease in a mammal, such as a human.

In another aspect of the invention, there is provided a pharmaceutical composition comprising: (a) a therapeutically efficacious amount of a compound of formula (I); and (b) a pharmaceutically acceptable excipient, for use in the treatment or prevention of a disease in a mammal, such as a human.

In another aspect of the invention, there is provided the use of a compound of formula (I) or a pharmaceutical composition comprising a compound of formula (I) for specifically binding to internal loop IIB of the RRE of the HIV-1 virus RNA.

In another aspect of the invention, there is provided the use of a compound of formula (I) or a pharmaceutical composition comprising a compound of formula (I) for inhibiting the interaction between RRE and the HIV-1 protein Rev.

In another aspect of the invention, there is provided the use of a compound of formula (I) or a pharmaceutical composition comprising a compound of formula (I) for inhibiting transcription mediated by the HIV-1 LTR promoter.

A further aspect of the invention relates to the use of a compound of formula (I) or a pharmaceutical composition comprising a compound of formula (I) for blocking HIV-1 replication in vivo.

A further aspect of the invention relates to the use of a compound of formula (I) or a pharmaceutical composition comprising a compound of formula (I) for inhibiting gram-positive and gram-negative bacteria and preventing and/or treating bacterial infections.

In yet a further aspect of the present invention, there is provided a compound of Formula (I) or pharmaceutical composition comprising said compound for preventing and/or treating HIV-1 infections and related diseases including, but not limited to, infections caused by other RNA viruses such as HIV-2 and other retroviruses, the virus of severe acute respiratory syndrome and other coronaviruses, hepatitis C virus, yellow fever virus, dengue virus, West Nile virus and other flaviviruses, poliovirus and other picornaviruses, influenza viruses and other orthomyxoviruses, the Ebola virus and other filoviruses, human parainfluenza virus and other paramyxoviruses, and rotavirus and other reoviruses; infectious or chronic diseases where these compounds may be used to modulate the function of RNA internal loops such as those present in human telomerases or the mRNAs of human oncogenes such as I-myc (relevant for the treatment of various cancer types including neuroblastoma amongst others), in the ribosomal subunits and riboswitches of bacteria (relevant for the treatment or prevention of infections caused by bacteria such as Staphilococcus aureus, Mycobacterium tuberculosis, Streptococcus pneumoniae, Streptococcus pyogenes, Haemophilus influenza, Neisseria meningitides or Pseudomonas aeruginosa amongst others) or in functional regions of viral RNA molecules such as the internal ribosome entry site or the 3'X domain of the hepatitis C virus (relevant for the treatment of diseases caused by this and other RNA viruses); infectious or chronic diseases responsive to inhibition of DNA transcription, such as inhibition of transcription promoted by the HIV-1 LTR (relevant for the treatment of HIV infections), or inhibition of transcription modulated by human transcription factors such as NF-κB, STAT factors or HMG-1 amongst others (relevant for the treatment of variety of human cancers, including prostate cancer, ovarian cancer, breast cancer, head and neck cancer, multiple myeloma and renal cell cancer); and infectious or chronic diseases where the compounds of the invention can be used as agonists or inhibitors of α-helical proteins in interaction with other biomolecules, such as the c-myc transcription factor in interaction with DNA and proteins like Max (relevant for the treatment of various cancer types including Burkitt lymphoma and colon or prostate cancer amongst others), Ap-1 and Sp-1 factors and steroid receptors in interaction with DNA (relevant for the treatment of hepatocarcinoma amongst other cancers) or the Rev and Gag proteins in interaction with the HIV-1 virus packaging signal RNA, or the Rev protein in interaction with other Rev monomers (relevant for the treatment of HIV infections). Other diseases where these compounds can be used as agonists or inhibitors of α-helical proteins in interaction with other biomolecules may also include for example herpes simplex virus infections, hypertension, psoriasis, asthma, autoimmune diseases including lupus (lupus erythematosus), multiple sclerosis and rheumatoid arthritis, fibromyalgia, neuronal disorders such as epilepsy, and neurodegenerative diseases including Alzheimer's disease and Parkinson's disease, among others.

It is a further object of the present invention a method of treatment or prevention of HIV-1 infections and related diseases in humans. Diseases include, but are not limited to, infections caused by other RNA viruses such as HIV-2 and other retroviruses, the virus of severe acute respiratory syndrome and other coronaviruses, hepatitis C virus, yellow fever virus, dengue virus, West Nile virus and other flaviviruses, poliovirus and other picornaviruses, influenza viruses and other orthomyxoviruses, the Ebola virus and other filoviruses, human parainfluenza virus and other paramyxoviruses, and rotavirus and other reoviruses; infectious or chronic diseases where these compounds may be used to modulate the function of RNA internal loops such as those present in human telomerases or the mRNAs of human oncogenes such as I-myc (relevant for the treatment of various cancer types including neuroblastoma amongst others), in the ribosomal subunits and riboswitches of bacteria (relevant for the treatment of infections caused by bacteria such as Staphilococcus aureus, Mycobacterium tuberculosis, Streptococcus pneumoniae, Streptococcus pyogenes, Haemophilus influenza, Neisseria meningitides or Pseudomonas aeruginosa amongst others), or in functional regions of viral RNA molecules such as the internal ribosome entry site or the 3'X domain of the hepatitis C virus (relevant for the treatment of diseases caused by this and other RNA viruses); infectious or chronic diseases responsive to inhibition of DNA transcription, such as inhibition of transcription promoted by the HIV-1 LTR (relevant for the treatment of HIV infections), or inhibition of transcription modulated by human transcription factors such as NF-κB, STAT factors or HMG-1 amongst others (relevant for the treatment of variety of human cancers, including prostate cancer, ovarian cancer, breast cancer, head and neck cancer, multiple myeloma and renal cell cancer); and infectious or chronic diseases where the compounds of the invention can be used as agonists or inhibitors of α-helical proteins in interaction with other biomolecules, such as the c-myc transcription factor in interaction with DNA and proteins like Max (relevant for the treatment of various cancer types including Burkitt lymphoma and colon or prostate cancer amongst others), Ap-1 and Sp-1 factors and steroid receptors in interaction with DNA (relevant for the treatment of hepatocarcinoma amongst other cancers) or the Rev and Gag proteins in interaction with the HIV-1 virus packaging signal RNA, or the Rev protein in interaction with other Rev monomers (relevant for the treatment of HIV infections). Other diseases where these compounds can be used as agonists or inhibitors of α-helical proteins in interaction with other biomolecules may also include for example herpes simplex virus infections, hypertension, psoriasis, asthma, autoimmune diseases including lupus (lupus erythematosus), multiple sclerosis and rheumatoid arthritis, fibromyalgia, neuronal disorders such as epilepsy, and neurodegenerative diseases including Alzheimer's disease and Parkinson's disease, among others.

In other aspects of the present invention, compounds according to the present invention may be used as agonists or antagonists in binding assays, and as analytical agents, among other uses.

The synthesis of the compounds of formula (I) represents another aspect of the invention. Compounds of the general formula (I) may be prepared by any suitable method known in the art and/or by the processes described below. It will be appreciated that where a particular stereoisomer of formula (I) is required, the synthetic processes described herein may be used with the appropriate homochiral starting material and/or isomers maybe resolved from mixtures using conventional separation techniques (eg. HPLC).

The compounds according to the invention may be prepared by sequential C—C bond formation via the palladium catalysed Suzuki coupling of halides, aryltriflates and boronic esters of the bilaterally substituted A, B and C rings. In this method, $R^1$, $R^2$, $R^5$, y $R^6$ of the final molecule of formula (I) are introduced by the halide derivatives of A and C and $R^3$ y $R^4$ are introduced by the boronic ester of B.

The present invention is intended to encompass all pharmaceutically acceptable ionized forms (e.g. salts) and solvates (e.g. hydrates) of the compounds under Formula I regardless of whether such forms and solvates are specified, as it is well known in the art that pharmaceutical agents in an ionized or solvated form may be used.

It will be appreciated that the compounds according to the invention can contain asymmetrically substituted carbon atoms. The presence of one or more asymmetric centres in a compound of formula I can give rise to stereoisomers and in each case the invention is to be understood to extend to all such stereoisomers, including enantiomers and diastereomers, and mixtures including racemic and non-racemic mixtures thereof, which may be obtained by methods known to those skilled in the art.

The compounds of Formula I may form organic and inorganic salts, for example, with inorganic or organic acids, e.g. hydrochloric acid, hydrobromic acid, fumaric acid, tartaric acid, citric acid, sulfuric acid, maleic acid, acetic acid, succinic acid, benzoic acid, palmitic acid, dodecanoic acid and acidic amino acids, such as glutamic acid, alkali metal hydroxides, e.g. sodium hydroxide, with amino acids, e.g., lysine or arginine. The salts formed with compounds under Formula I provided that they are pharmaceutically acceptable may be used in the present invention. Such salts and corresponding solvates also fall within the scope of the present invention.

Prodrugs of the compounds of Formula I are also the subject of the present invention. As is known in the art, prodrugs are altered in vivo and become a compound of the present invention. All standard methods of using the compounds of the present invention are intended, whether or not prodrug delivery is specified, to encompass the administration of a prodrug that is converted in vivo to a compound according to the present invention.

A variety of routes of administration of the compounds and compositions of the present invention are possible including, but not necessarily limited to parenteral (e.g., intravenous, intra-arterial, intramuscular, subcutaneous injection), oral (e.g., dietary or by inhalation), topical, nasal, vaginal, rectal, or via slow release micro-carriers, depending on the condition to be treated. Oral, parenteral and intravenous are preferred modes of administration. Vaginal administration, for example, with a vaginal gel formulation is also preferred. The formulation of the compounds of the present invention to be administered will vary according to the route of administration selected (e.g., solution, emulsion, gel, aerosol, capsule). Further dosage forms according to the present invention are, for example, solutions, suspensions, ointments, creams, pastes, gels, tinctures, lip-sticks, drops, syrups, aerosols and sprays.

A suitable composition of the present invention comprising the compound or compounds of Formula I can be prepared in a physiologically acceptable vehicle or carrier and can contain optional adjuvant and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See Remington's Pharmaceutical Science, $16^{th}$ Edition, Mack, Ed. (1980)).

Preferred compositions for parenteral administration are under the form of solutions, suspensions, emulsions, dispersions and lyophilized compositions of the compounds of the invention, preferably in the form of isotonic aqueous solutions, dispersions, emulsions or suspensions. These compositions are preferably sterile, either being processed in a sterile environment during their whole preparation process or by being sterilized in the end of said process. Furthermore, their manufacture is usually carried out under sterile conditions, as is the filling, for example, into ampoules or vials, and the sealing of the containers. These compositions may be ready to apply or be presented under solid form (for example as a lyophilizate) requiring reconstitution prior application.

Parenteral compositions according to the present invention may comprise excipients, for example vehicles, stabilizers (reducing agents, anti-oxidants and/or sequestering agents), buffering agents, preservatives, isotonising agents, emulsifiers, solubilisers, viscosity increasing agents, and/or bulking agents and are prepared by conventional processes well known to those knowledgeable of the art.

A preferred route of administration is oral. Pharmaceutical oral compositions in solid form (tablets, soft capsules, hard capsules or any other) according to the present invention comprise excipients, provided they are compatible with the active ingredient of the composition, including, but not limited to, diluents, binders, disintegrants, surfactants, glidants, lubricants, antioxidants or free radicals sequestrants, coating components, opacifiers or plasticisers.

If a solid composition in the form of tablets is prepared, the compound of the present invention can be mixed with a pharmaceutical vehicle, examples of which include silica, starch, lactose, magnesium stearate and talc. The tablets can be coated with sucrose or another appropriate substance or they can be treated so as to have a sustained or delayed activity and so as to release a predetermined amount of active ingredient continuously. Gelatin capsules can be obtained by mixing the active ingredient with a diluent and incorporating the resulting mixture into soft or hard gelatin capsules. A syrup or elixir can contain the active ingredient in conjunction with a sweetener, an antiseptic (e.g. methylparaben and/or propylparaben), a flavouring, and an appropriate color. Water-dispersible powders or granules can contain the active ingredient mixed with dispersants or wetting agents or with suspending agents such as, polyvinylpyrrolidone, as well as with sweeteners or taste correctors.

The term "pharmaceutically acceptable carrier" as used in the present invention includes any solvent, dispersion media, coatings, isotonic and absorption delaying agents, and the like which are compatible with the activity of the compounds and are physiologically acceptable to the subject.

"Effective amount" as used in the present invention includes the amount of the compound or a pharmaceutically acceptable salt thereof, ester, isomer, solvate, or prodrug thereof which allows it to perform its intended function, i.e., treatment of HIV-1 infections and other diseases. Other diseases include, but are not limited to diseases caused by other RNA viruses and by gram-positive and gram-negative bacteria, infectious or chronic diseases responsive to inhibition of DNA transcription, or infectious or chronic diseases where these compounds may be used to modulate the function of RNA internal loops, or as agonists or inhibitors of α-helical proteins in interaction with other biomolecules.

A therapeutically effective amount of the active substance of the present invention can be administered by an appropriate route in a single dose or multiple doses. The therapeutically effective amount will depend upon a number of factors, including biological activity, mode of administration, frequency of treatment, type of concurrent treatment, if any, age, body weight, sex, general health, severity of the condition to be treated, as well as appropriate pharmacokinetic properties. One skilled in the art can determine the appropriate dosage based on the above factors.

The compounds of the invention may be administered initially in a suitable dosage that may be adjusted as required, depending on the clinical response. In general, satisfactory results may be obtained when the compounds of the invention are administered to a human at an approximate daily dosage (measured as the solid form) of about 0.05 to 100 mg/Kg of body weight. An approximate preferred dose ranges between about 0.1 and 50 mg/Kg/day, more preferably between about 1-20 mg/Kg/day.

The compound can be administered in the form of pharmaceutical compositions comprising the compound once a day or at different times within the day, prophylactically or therapeutically, preferably in an amount effective against HIV-1 infection or the related disease, to a mammal, for example a human, requiring such treatment. In the case of an individual having a body weight of about 75 kg, the daily dose of the mixture administered is from approximately 0.004 g to approximately 7.5 g, preferably from approximately 0.075 g to approximately 0.150 g, of a compound of Formula I or a pharmaceutically acceptable salt, ester, isomer, solvate, or prodrug thereof.

The pharmaceutical compositions of the present invention can comprise from 0.01% to 100% by weight of a mixture of a compound of formula I, typically from approximately 0.05% to approximately 80%.

The pharmaceutical compositions of the present invention may, if desired, be formulated so as to provide an immediate or modified release of the active ingredient after administration to the patient.

Typically, unit dose administration forms according to the present invention can comprise from approximately 0.05% to approximately 80% of the compound of formula I.

Unit dose forms according to the present invention refer to, for example, coated and uncoated tablets, microcapsules, soft and hard capsules, pellets, powdered doses, ampoules, vials and suppositories.

The present invention relates especially to the use of a compound of formula I or a pharmaceutical acceptable salt, ester, isomer, solvate and/or prodrug, as such or in the form of a pharmaceutical formulation with at least one pharmaceutically acceptable carrier for the therapeutic and also prophylactic treatment of HIV-1 infections and other diseases. Other diseases include, but are not limited to, diseases caused by other RNA viruses and by gram-positive and gram-negative bacteria, infectious or chronic diseases responsive to inhibition of DNA transcription, or infectious or chronic diseases where these compounds may be used to modulate the function of RNA internal loops, or as agonists or inhibitors of α-helical proteins in interaction with other biomolecules.

Obtaining the Compounds of the Present Invention
1.—Structure-Based Design of RRE-Rev Inhibitors.

Based on the three-dimensional structure of $Rev_{34-50}$ bound to internal loop IIB of the RRE(7) (FIG. 1a), design of organic ligands mimicking the three-dimensional distribution of the $Rev_{34-50}$ helix side chains in its complex with the loop was aimed. In this respect, some reports had shown that tris-ortho-substituted p-terphenyl molecules could mimic one face of a α-helical peptide by adopting a staggered conformation that reproduced the angular orientation of three α-helix side chains, and that some of these molecules were able to inhibit protein-protein interactions(15). For the purpose of the present invention it was envisioned that introduction of substituents on both sides of a p-terphenyl scaffold would ensure a 360° side-chain projection similar to that observed in the IIB-$Rev_{34-50}$ complex, where two thirds of the α-helix are surrounded by RNA. An in silico conformational analysis of an hexakis-ortho-substituted p-terphenyl model molecule confirmed this prediction: while the ortho orientation of the substituents induced a staggered conformation, the presence of substituents on both sides of the rings ensured a broad side-chain projection in space. The hypothesis that these molecules might selectively bind to the RRE loop by mimicking the $Rev_{34-50}$ α-helix was supported by docking p-biphenyl and p-terphenyl ligands containing different substitution patterns into the RRE structure(7) (PDB codes 1ETF and 1ETG). As expected, the best results were obtained for hexakis-ortho-substituted p-terphenyl molecules (compounds under Formula I) whose binding poses approximately reproduced the orientation of $Rev_{34-50}$ in its complex with the RRE. After testing several possibilities for the lateral substituents in additional calculations, it was found that 2-amino-ethyl chains were synthetically-accessible and well suited to interact with the sugar-phosphate backbone of the RRE internal loop.

2.—Synthesis of Bilaterally-Substituted p-Biphenyl and p-Terphenyl Compounds.

On the basis of the structure-based computational predictions, applicants set out to synthesize p-biphenyl and p-terphenyl molecules with bilateral substitutions on the benzene rings, which correspond to compounds of Formula I. The syntheses were based on sequential palladium-based Suzuki couplings (16-18) of aryl halides and aryl triflates with aryl boronic esters, as shown in the following scheme:

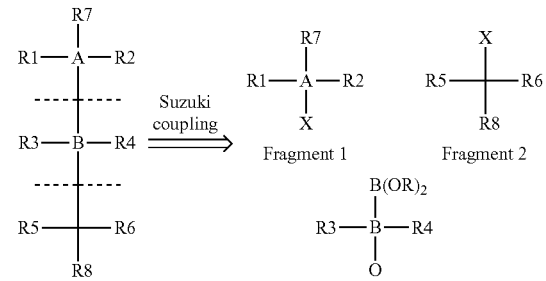

Preferred compounds of the invention were prepared according to the following scheme:

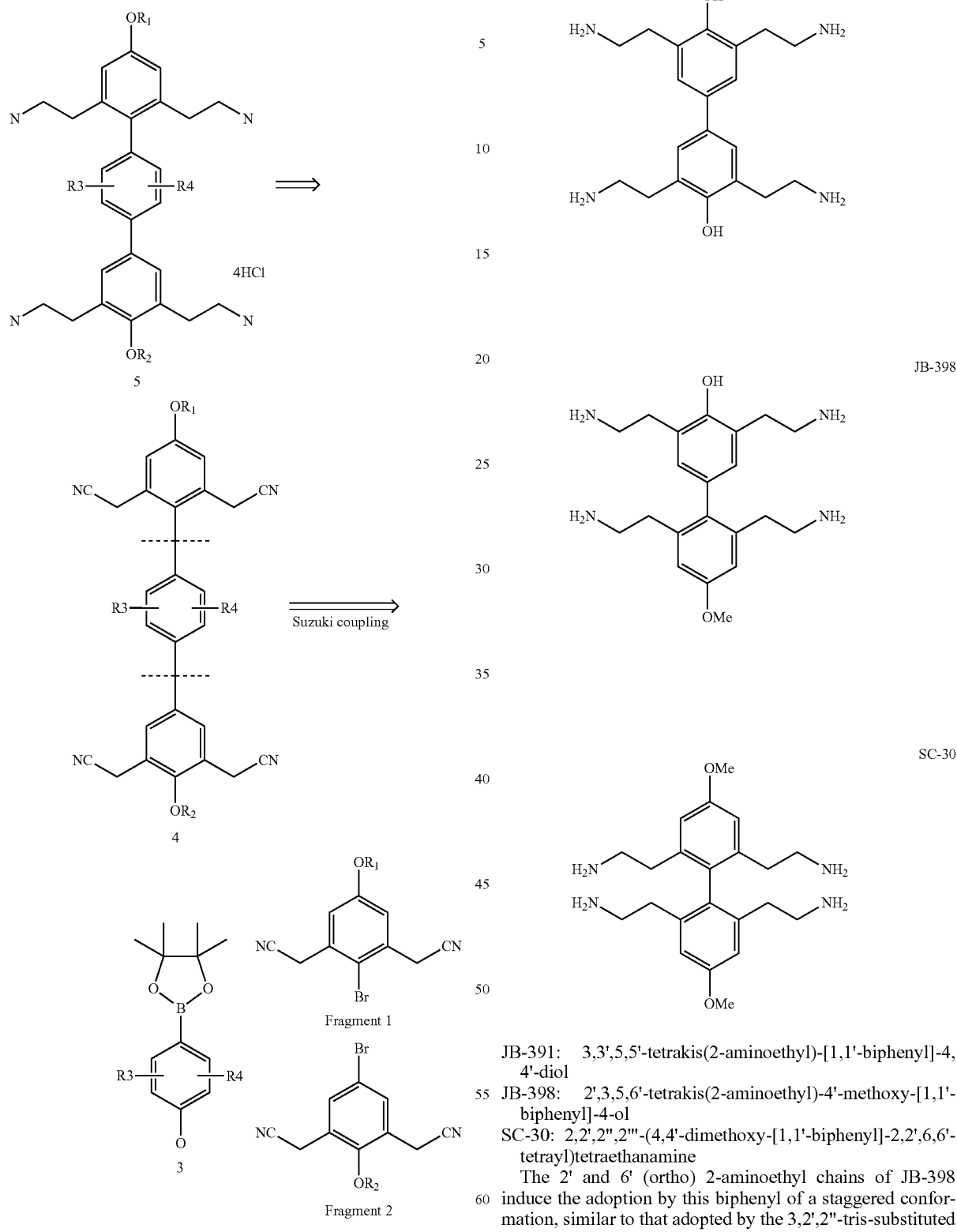

The following group of tetrakis (2-aminoethyl) 1-1' biphenyls where the 2-aminoethyl side-chains occupied bilateral 3,5 and 2',6' (JB-398), 2,6 and 2',6' (SC-30), and 3,5 and 3',5' (JB-391) positions was first generated:

JB-391: 3,3',5,5'-tetrakis(2-aminoethyl)-[1,1'-biphenyl]-4,4'-diol
JB-398: 2',3,5,6'-tetrakis(2-aminoethyl)-4'-methoxy-[1,1'-biphenyl]-4-ol
SC-30: 2,2',2'',2'''-(4,4'-dimethoxy-[1,1'-biphenyl]-2,2',6,6'-tetrayl)tetraethanamine The 2' and 6' (ortho) 2-aminoethyl chains of JB-398 induce the adoption by this biphenyl of a staggered conformation, similar to that adopted by the 3,2',2''-tris-substituted p-terphenyls that behave as α-helix mimics(15). The steric hindrance is maximized in SC-30, where all four 2-aminoethyl chains occupy ortho positions relative to the carbons joining the two benzene rings. In contrast, the bilateral 2-aminoethyl chains of JB-391 are meta, so that this molecule can adopt a planar conformation.

The following terphenyl molecules were synthesized according to the method previously described:
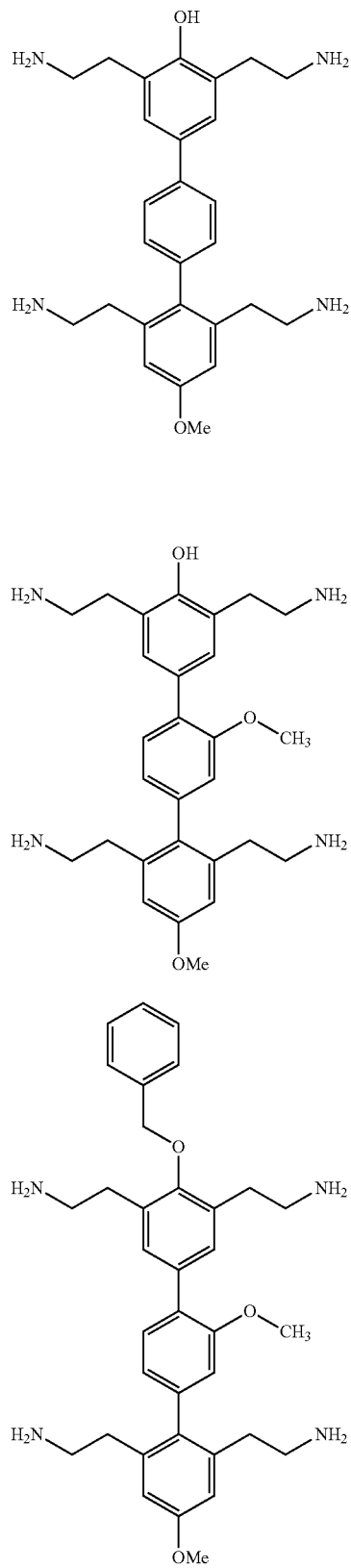
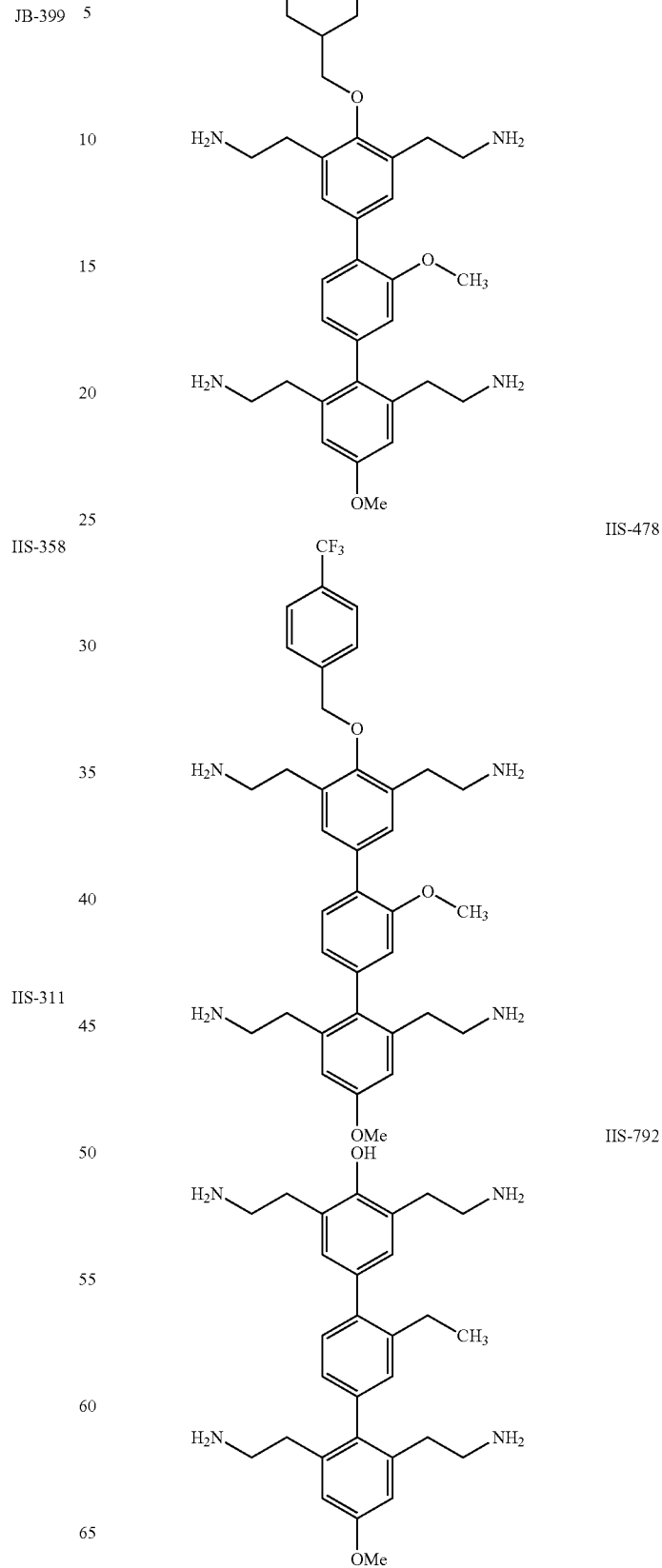

IIS-758

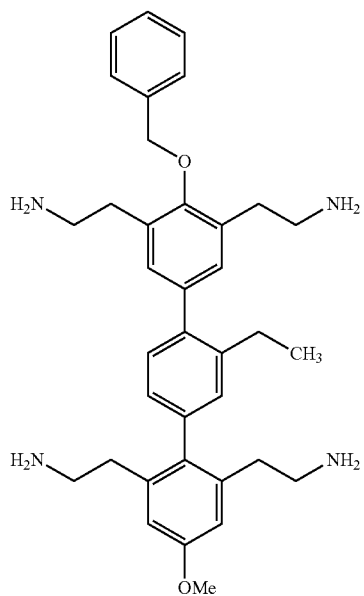

IIS-420

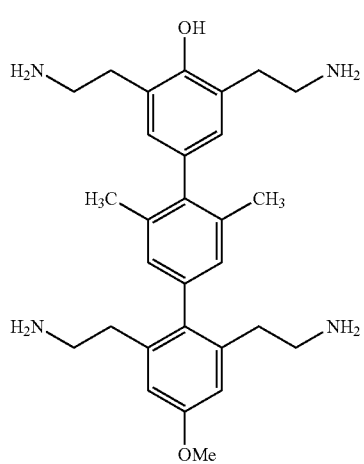

IIS-375

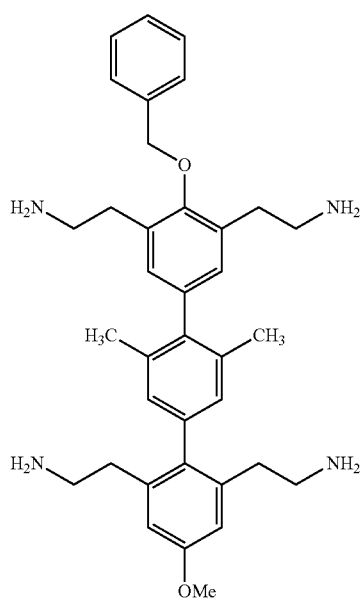

IIS-806

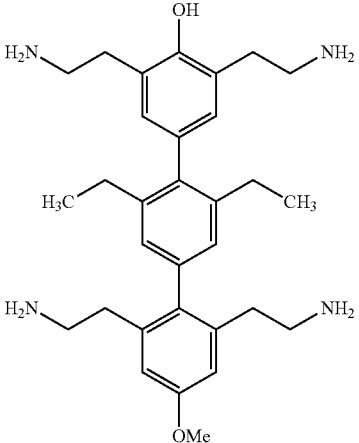

IIS-771

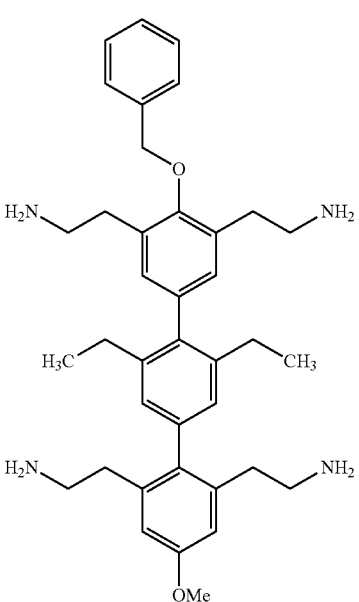

JB-399: 2",3,5,6"-tetrakis(2-aminoethyl)-4"-methoxy-[1,1': 4',1"-terphenyl]-4-ol IIS-358: 2",3,5,6"-tetrakis(2-aminoethyl)-2',4"-dimethoxy-[1,1':4',1"-terphenyl]-4-ol IIS-311: 2,2',2",2'''-(4"-(benzyloxy)-3',4-dimethoxy-[1,1':4', 1"-terphenyl]-2,3",5",6-tetrayl)tetraethanamine IIS-478: 2,2',2",2'''-(3',4-dimethoxy-4"-((4-(trifluoromethyl)benzyl)oxy)-[1,1':4',1"-terphenyl]-2,3",5",6-tetrayl) tetraethanamine IIS-530: 2,2',2",2'''-(4"-(cyclohexylmethoxy)-3',4-dimethoxy-[1,1':4',1"-terphenyl]-2,3",5",6-tetrayl)tetraethanamine IIS-420: 2",3,5,6"-tetrakis(2-aminoethyl)-4"-methoxy-2',6'-dimethyl-[1,1':4',1"-terphenyl]-4-ol IIS-375: 2,2',2",2'''-(4"-(benzyloxy)-4-methoxy-3',5'-dimethyl-[1,1':4',1"-terphenyl]-2,3",5",6-tetrayl)tetraethanamine IIS-792: 2",3,5,6"-tetrakis(2-aminoethyl)-2'-ethyl-4"-methoxy-[1,1':4',1"-terphenyl]-4-ol IIS-758: 2,2',2",2'''-(4"-(benzyloxy)-3'-ethyl-4-methoxy-[1, 1':4',1"-terphenyl]-2,3",5",6-tetrayl)tetraethanamine IIS-806: 2",3,5,6"-tetrakis(2-aminoethyl)-2',6'-diethyl-4"-methoxy-[1,1':4',1"-terphenyl]-4-ol IIS-711: 2,2',2'',2'''-(4''-(benzyloxy)-3',5'-diethyl-4-methoxy-[1,1':4',1''-terphenyl]-2,3'',5'',6-tetrayl)tetraethanamine The first terphenyl molecule (JB-399) contained four 2-aminoethyl side-chains occupying the 3,5 and 2'',6'' bilateral positions of the two terminal benzene rings and lacked substituents in the central ring. In this case, a staggered conformation is expected for the 4'-1'' bond joining the second and third benzenes, but not for the other one. The second series of similar 3,5,2'',6'' tetrakis (2-aminoethyl) terphenyls contained a single methoxy (IIS-358, IIS-311, IIS-478 and IIS-530) or ethyl (IIS-792 and IIS-771) substituent in the 2' position of the central ring. These terphenyls will adopt a staggered conformation around both benzene-benzene bonds, and contained different groups in the para carbon of the first ring: 4-hydroxyl (IIS-358 and IIS-792), 4-benzyl (IIS-311 and IIS-758), 4-p-fluoro-bencyl (IIS-478) or 4-cyclohexyl (IIS-530). The third series of 3,5,2'',6'' tetrakis (2-aminoethyl) terphenyls contained two methyl (IIS-420 and IIS-375) or ethyl (IIS-806 and IIS-771) groups occupying the 2' and 6' bilateral positions of the central ring, as well as 4-hydroxyl (IIS-420 and IIS-806) or 4-benzyl (IIS-375 and IIS-771) para substituents. These molecules are 3,5,2',2'',6',6'' hexakis-substituted p-terphenyl molecules containing bilateral groups in all three rings, and were predicted by the structure-based calculations to be the best $Rev_{34-50}$ mimics.

Compound Functionality

1.—Bilaterally-Substituted p-Terphenyl Compounds Bind Specifically to the RRE with Low Stoichiometry The interaction of these biphenyl and terphenyl compounds with the RRE RNA hairpin (SEQ. ID. No 1) was analysed using surface plasmon resonance (SPR) experiments(19). In addition to the RRE, two control $RRE_c$ (SEQ. ID. No 2) and $TAR_c$ (SEQ. ID. No 3) hairpins were also immobilised on the chips. In the $RRE_c$ hairpin the internal loop forming the Rev high-affinity binding site is replaced with a G:G opposition, whereas in the $TAR_c$ hairpin this loop is substituted with the HIV-1 Tat-binding UCU bulge(20). In this way, applicants could simultaneously assess the interaction of each ligand with RRE, $RRE_c$ and $TAR_c$, obtaining important information about binding selectivity. In addition, the SPR methodology allows deduction of binding stoichiometries, which are likewise related to the specificity of the interaction between a ligand and a given RNA species. These are key considerations in the nucleic acid recognition field(4, 5, 14).

The applicants benchmarked the SPR methodology by analysing the interaction of RRE with a TRQARRN-RRRRWRERQRAAAAR peptide, hereafter called revp (SEQ ID. No. 4), as well as the RRE-binding antibiotic neomycin B, which was used as a reference. revp contains the arginine-rich $Rev_{34-50}$ residue tract (TRQARRN-RRRRWRERQR) forming the α-helix that is critical for interaction with the RRE(21). For the RRE-revp interaction, the binding curves were best described with a one-site model and indicated an equilibrium dissociation constant $K_d$ of 4.2±3.4 nM together with a 1:1 binding stoichiometry. This means that a single molecule of revp interacts with one high-affinity site in the RRE hairpin, formed by internal loop IIB(7). The specificity of the RRE:revp interaction was quantified by calculating the $K_d(RRE_c)/K_d(RRE)$ and $K_d(TAR_c)/K_d(RRE)$ ratios, which were 14.5 and 4.4, respectively. The revp $K_d$ obtained by SPR was in very good agreement with the $K_d$'s reported in the literature for similar peptides(22, 23). For neomycin B, the binding curves were best described with a two-site model, and we obtained an equilibrium dissociation constant $K_d$ of 2.4±1.1 μM for three molecules binding to the higher affinity site. These results also coincided well with the $K_d$ values and binding stoichiometries previously reported in the literature(23). With $K_d(RRE_c)/K_d(RRE)$ and $K_d(TAR_c)/K_d(RRE)$ ratios of 0.9 and 2.3, the specificity of the RRE:neomycin interaction was rather poor, as previously reported(24).

Figure 2:
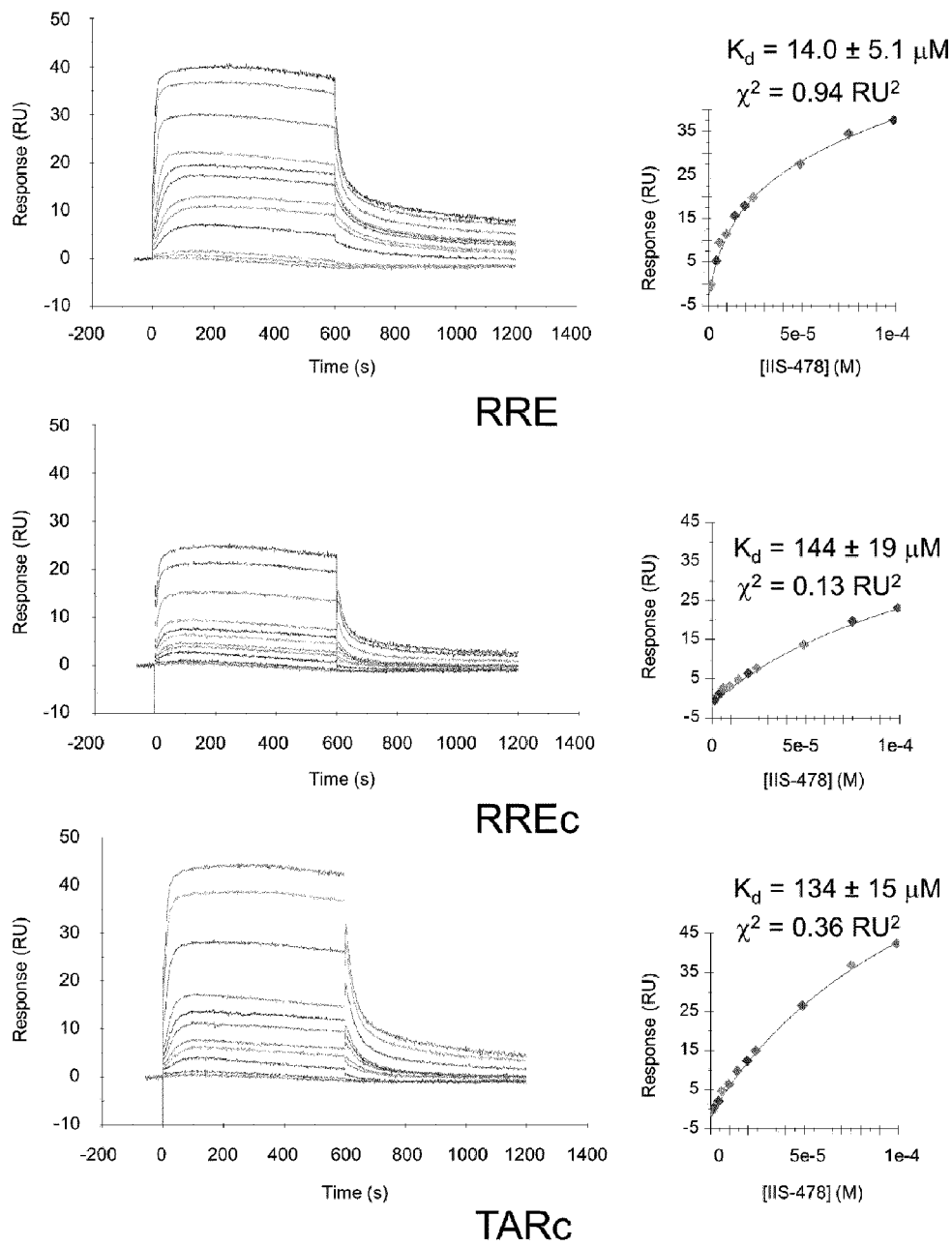
FIG. 2 represents SPR (Surface Plasmon Resonance) analyses of the interaction between a bilaterally-substituted p-terphenyl (IIS-478) and RNA hairpins RRE, RREc and TARc. Representative SPR sensorgrams (left) and steady-state equilibrium binding curves (right) for the RRE:IIS-478 (top), RREc:IIS-478 (middle) and TARc:IIS-478 (bottom) interactions, measured at 25° C. and pH 7.4. The plotted ligand concentrations range from 0.1 to 100 μM. Similar quantities of RNA hairpin (approximately 300 RUs) were immobilized on the SPR chips. The binding parameters and $\chi^2$ values obtained from curve fitting are indicated on the graphs.

When the biphenyl and terphenyl ligands were evaluated with these experiments, the best results were obtained for terphenyl molecules, some of which were capable of binding to the RRE hairpin with affinities of 8 μM and binding stoichiometries of one to two molecules for the higher affinity site (FIG. 2 and Table 1). The terphenyl compounds containing a relatively polar group (methoxy) in the central benzene ring, particularly IIS-358, IIS-311 e IIS-478, gave rise to the best specificity data, with $K_d(RRE_c)/K_d(RRE)$ and $K_d(TAR_c)/K_d(RRE)$ ratios of up to 10.3 and 9.6, respectively (Table 1 and FIG. 2), comparable to those obtained with the revp peptide (14.5 and 4.4). Terphenyl compounds containing a hydrophobic group (methyl or ethyl) in the central benzene and a 4-OH group showed higher affinity for the RRE hairpin.

TABLE 1

RRE-biphenyl and RRE-terphenyl interaction parameters measured by SPR experiments at 25° C. RRE equilibrium dissociation constants ($K_d$), RRE binding stoichiometries (n), and RRE binding specificities relative to the control $RRE_c$ and $TAR_c$ hairpins, quantified as $K_d(RRE_c)/K_d(RRE)$ and $K_d(TAR_c)/K_d(RRE)$.

| compound[a] | $K_d(RRE)$ (M ·10⁶) | n[s] (RRE) | $\frac{K_d(RRE_c)}{K_d(RRE)}$ | $\frac{K_d(TAR_c)}{K_d(RRE)}$ |
|---|---|---|---|---|
| JB-398 | 31.1 ± 5.0 | 4.3[1] ± 0.3 | — | 3.7 |
| SC-30 | >100 | — | — | — |
| JB-399[b] | 14.4 ± 6.8 | 0.7[1] ± 0.1 | — | 11.7 |
| IIS-358 | 13.0 ± 9.0 | 1.1[2] ± 1.0 | 1.9 | 6.0 |
| IIS-311 | 9.4 ± 5.7 | 1.3[2] ± 0.6 | 4.9 | 3.2 |
| IIS-478[c] | 14.0 ± 5.1 | 1.4[2] ± 0.4 | 10.3 | 9.6 |
| IIS-530[b] | 46.2 ± 32.0 | 2.5[1] ± 1.1 | 1.3 | 4.0 |
| IIS-792[d] | 8.1 ± 1.8 | 1.3[1] ± 0.1 | 1.2 | 1.6 |
| IIS-758[d] | 16.7 ± 1.6 | 4.6[1] ± 0.2 | 1.3 | 2.0 |
| IIS-806[d] | 8.1 ± 1.1 | 2.1[1] ± 0.1 | 1.1 | 1.3 |
| IIS-771[d] | 17.6 ± 1.8 | 2.7[1] ± 0.1 | 1.0 | 1.7 |

[a]All binding curves were fitted with either one-site or two-site binding models (indicated with s = 1 or s = 2 superscripts). When s = 2, the $K_d$ and n values are those of the high affinity site. The data were obtained at pH 6.3 except where indicated.
[b]Values determined using a ligand concentration range of 0.1-25 μM.
[c]Values determined at pH 7.4. Similar values of $K_d$, n[s] and $K_d(RRE_c)/K_d(RRE)$ were obtained at pH 6.25: 12.1 ± 3.1 μM, 2.1² ± 0.4 molecules and 10.2, respectively.
[d]Values determined at pH 7.4 using a ligand concentration range of 0.1-25 μM.

2.—NMR Spectroscopy Demonstrates a Specific Interaction Between the RRE Internal Loop and Bilaterally-Substituted Terphenyl Ligands.

Figure 3:
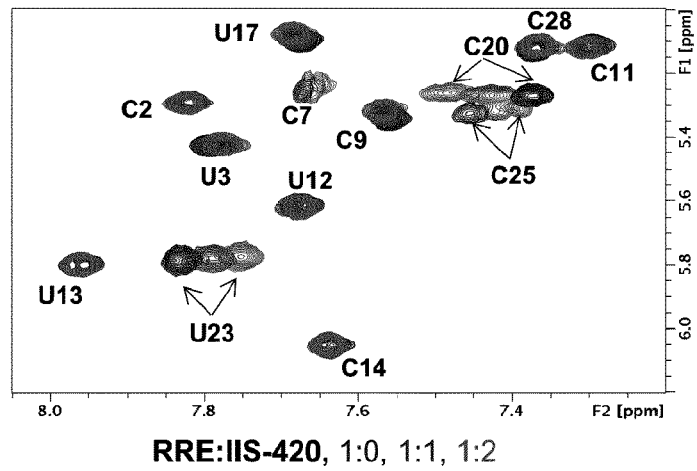
FIG. 3 represents NMR spectra of representative complexes of the RRE RNA hairpin with biphenyl and terphenyl molecules. The assignments of the aromatic H5-H6 TOCSY regions (60 ms mixing time, 27° C.) of the RRE:IIS-420, RRE:IIS-806 and RRE:JB-398 interactions are shown. RRE pyrimidine H5-H6 crosspeaks are labelled with residue name and number. In all cases, the unbound RRE spectra (1:0) is superposed on the spectra of complexes with increasing RRE:ligand molar ratios.
Figure 3:
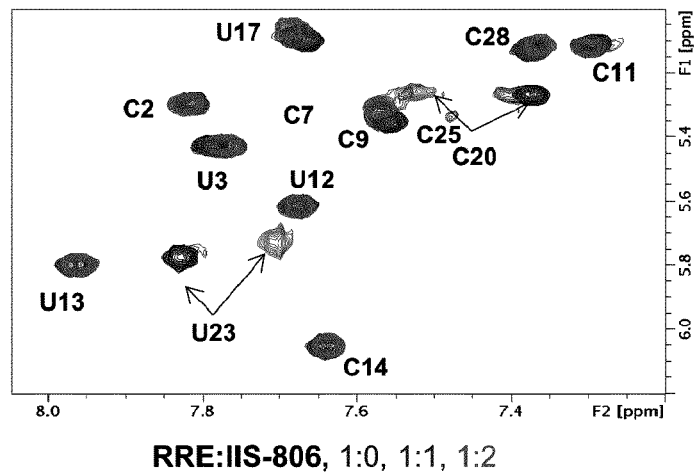
Figure 3:
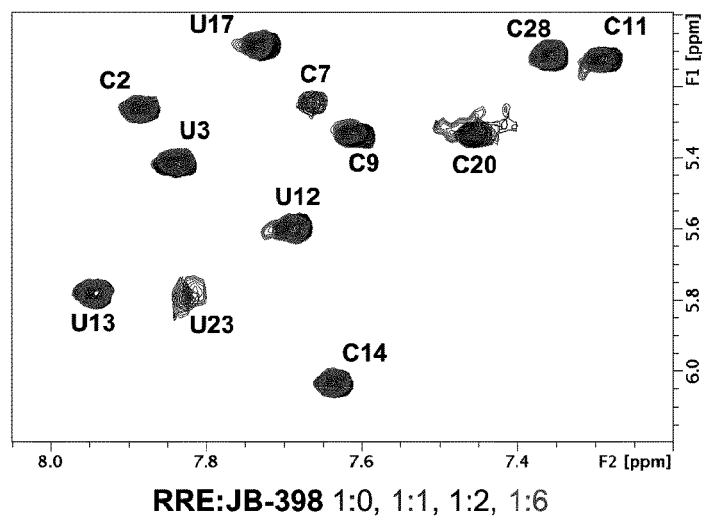

The interaction between the RRE hairpin (SEQ. ID. No 1) and biphenyl and terphenyl compounds was also analysed using two-dimensional NMR spectroscopy (FIG. 3). These experiments were useful to examine the strength of the interactions and the location of the binding sites, and revealed significant differences among the different ligands. The biphenyl JB-398 required a high RRE:ligand molar ratio (1:6) to produce detectable changes in the RRE TOCSY spectrum (FIG. 3, bottom), whereas JB-391, SC-30and neomycin B induced chemical shift perturbations in stem nucleotides outside the internal loop. These are indications of weak and unspecific binding, respectively.

In contrast, terphenyl molecules induced chemical shift changes in the internal loop and adjacent nucleotides only, particularly C20, U23 and C25 (FIG. 3), and these shifts were apparent at lower ratios. The shift variations were more pronounced for terphenyls molecules containing hydrophobic groups (methyl and ethyl) in the central benzene ring. JB-399 and the terphenyls containing a more polar group (methoxy) in the central ring, like IIS-358 and IIS-311, resulted in similar but less pronounced variations. The terphenyls that gave rise to the greatest RNA chemical shift variations and sharper complex resonances were IIS-420 and IIS-806, which contain two bilateral methyl or ethyl groups, respectively, in positions 2' and 6' of the central benzene (FIG. 3, top and middle). The RRE loop was titrated with two molar equivalents of these compounds. These results are consistent with the dissociation constants and binding stoichiometries determined by SPR experiments (Table 1).

Figure 4:
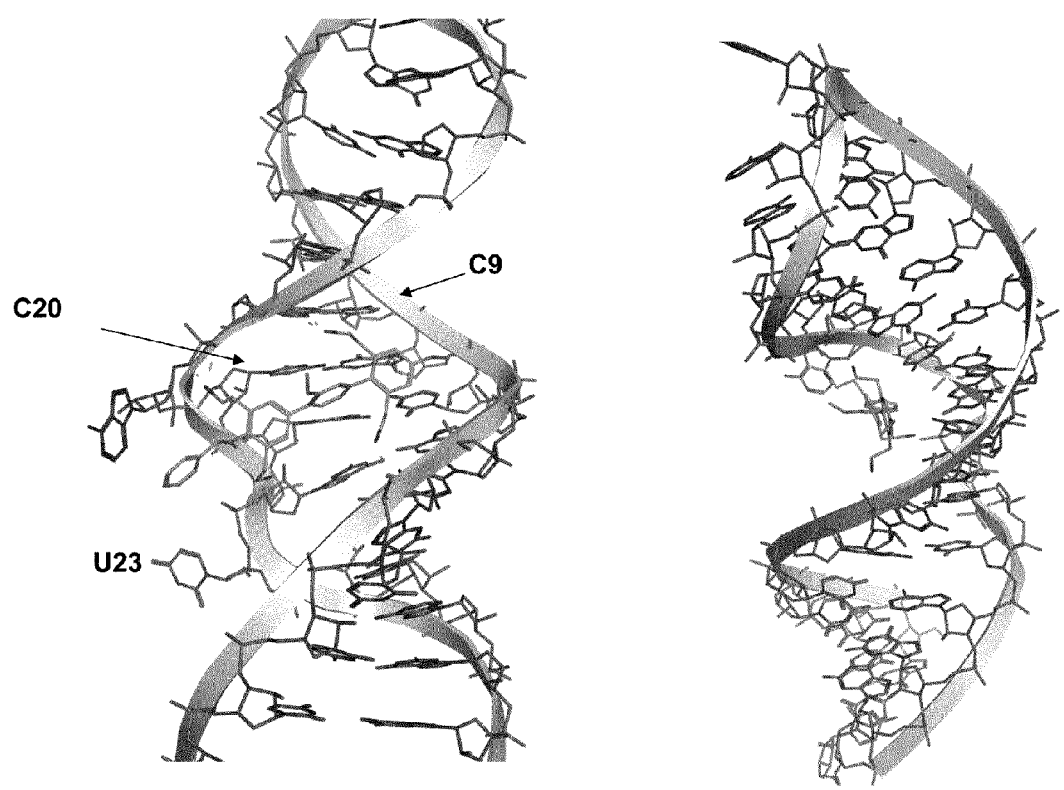
FIG. 4 represents an NMR-based computational model of an RRE:IIS-311 complex, built from the three-dimensional structure of RRE (PDB 1ETF) (7).

The fact that only nucleotides located in the loop or adjacent positions are affected by the interaction clearly indicates that the terphenyl ligands selectively bind to the internal loop within the RRE hairpin (FIG. 3). Moreover, weak intermolecular NOEs between terphenyl hydrogens and RNA protons located in the major groove were detected in the IIS-420 and IIS-806 complexes. These contacts indicate that the interaction with the RRE loop takes place from the major groove, as is the case with $Rev_{34-50}(7)$, confirming that these bilaterally-substituted terphenyls ligands occupy the binding site of $Rev_{34-50}$ in the RRE RNA (FIG. 4). Examination of the NOESY spectra of the best complexes also revealed that IIS-420 and IIS-806 induce conformational changes in the RRE similar to those brought about by $Rev_{34-50}$: this was indicated by a decrease in the intensity of the intraresidue H8-H1' NOE of G22: this guanine adopts a syn conformation in the unbound RRE loop that becomes anti upon both $Rev_{34-50}(25)$ and terphenyl ligand binding.

3.—Biphenyl and Terphenyl Ligands Inhibit the RRE-$Rev_{34-50}$ Interaction In Vitro.

Using an assay based on fluorescence anisotropy, we evaluated the capacity of biphenyl and terphenyl ligands to inhibit the interaction between RRE and $Rev_{34-50}$. An FITC-labelled GTRQARRNRRRRWRERQRAAAAR peptide (hereafter identified as frevp with SEQ ID. No. 5) and the RNA hairpin RRE (SEQ. ID. No 1) were used for these experiments. The results are shown in Table 2 and FIG. 5.

This experiment was validated by measuring the $IC_{50}$ and $K_i$ values of the revp peptide and the reference antibiotic neomycin B. The $K_i$ inhibition constant obtained for revp (4.1±0.8 nM) was in excellent agreement with the $K_d$ equilibrium dissociation constant independently determined by SPR (4.2±3.4 nM). Neomycin's Ki, 2.0±0.2 μM (obtained assuming that one ligand molecule is responsible for the observed frevp displacement), also coincided very well with the SPR $K_d$ (2.4±1.1 μM) and with $K_i$ values previously reported in the literature(23).

Figure 5:
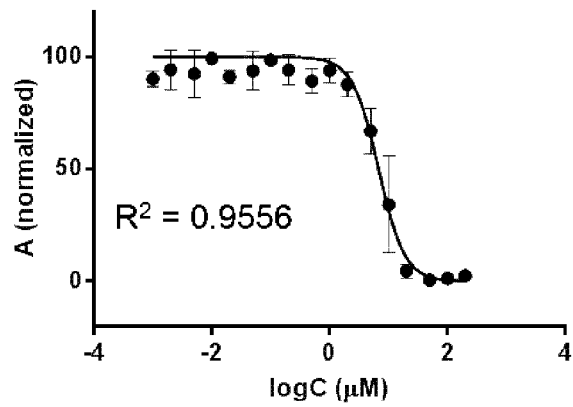
FIG. 5 represents inhibition of the RRE-$Rev_{34-50}$ interaction by terphenyls IIS-420 and IIS-375 and the reference antibiotic neomycin B, measured in vitro using a displacement assay based on fluorescence polarization. In the graphs, normalized anisotropy is plotted against the logarithm of compound concentration (μM), and the $R^2$ values of the fits used to obtain the $IC_{50}$ data are indicated.
Figure 5:
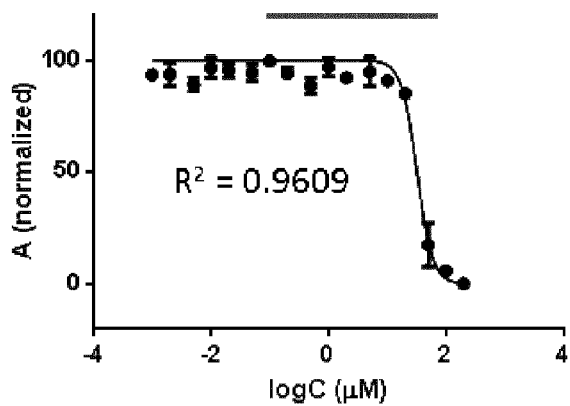
Figure 5:
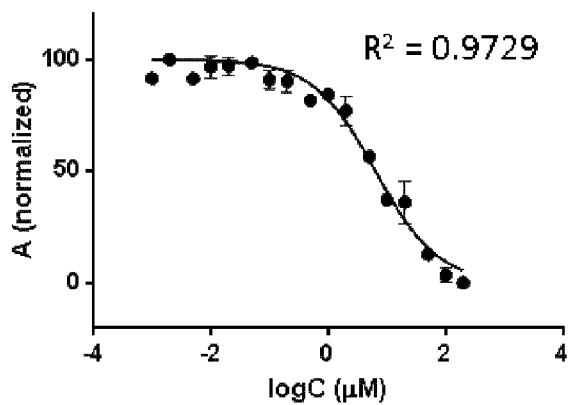

The terphenyl IIS-420, with an $IC_{50}$ value of 6.8 μM, was the most potent inhibitor, followed by JB-399 and other terphenyl molecules having methyl or ethyl groups in the central benzene (FIG. 5 and Table 2). Terphenyl molecules containing a single substituent in the central benzene, particularly those belonging to the more polar methoxy series, exhibited higher $IC_{50}$'s. The biphenyl molecules JB-391 and JB-398, with $IC_{50}$ values of 7.7 and 22.1 μM respectively, were surprisingly potent in this assay. However, these molecules interact poorly with the RRE loop (e.g. FIG. 3, bottom) and it is therefore likely that they inhibit the RRE-frevp interaction through a different mechanism.

TABLE 2

RRE-$Rev_{45-50}$ 50% inhibitory concentrations of biphenyl and terphenyl molecules and neomycin B, measured by fluorescence polarization experiments at 25° C.

| compound | $IC_{50}{}^a$ (M · 10$^6$) |
|---|---|
| JB-391 | 7.7 ± 0.8 |
| JB-398 | 22.1 ± 5.8 |
| SC-30 | 308.7 ± 68.9 |
| JB-399 | 23.4 ± 3.6 |
| IIS-358 | 808.0 ± 461.7 |
| IIS-311 | 162.2 ± 117.6 |
| IIS-478 | 232.0 ± 32.7 |
| IIS-530 | 75.5 ± 39.9 |
| IIS-792 | 93.6 ± 24.4 |
| IIS-758 | 78.1 ± 6.5 |
| IIS-806 | 56.4 ± 13.5 |
| IIS-771 | 77.2 ± 15.5 |
| IIS-420 | 6.8 ± 0.5 |
| IIS-375 | 32.2 ± 2.3 |

$^a$All $IC_{50}$ values were obtained with 60 nM RRE and 10 nM frevp. The FP experiments were repeated at least two times, and the table shows the standard deviation of independent experiments except for IIS-311, IIS-358 and IIS-530, where the standard error of fitting a representative curve is indicated. No RRE-$Rev_{45-50}$ inhibition was detected for the fragments 2,6-(2aminoethyl)-4-methoxy-1-bromo-benzene and 2,6-(2aminoethyl)-4-benzyloxy-1-bromo-benzene, used as controls.

4.—RRE-$Rev_{34-50}$ Inhibitors Block HIV-1 Replication In Vivo and Exert this Effect Post-Transcriptionally.

Figure 6A:
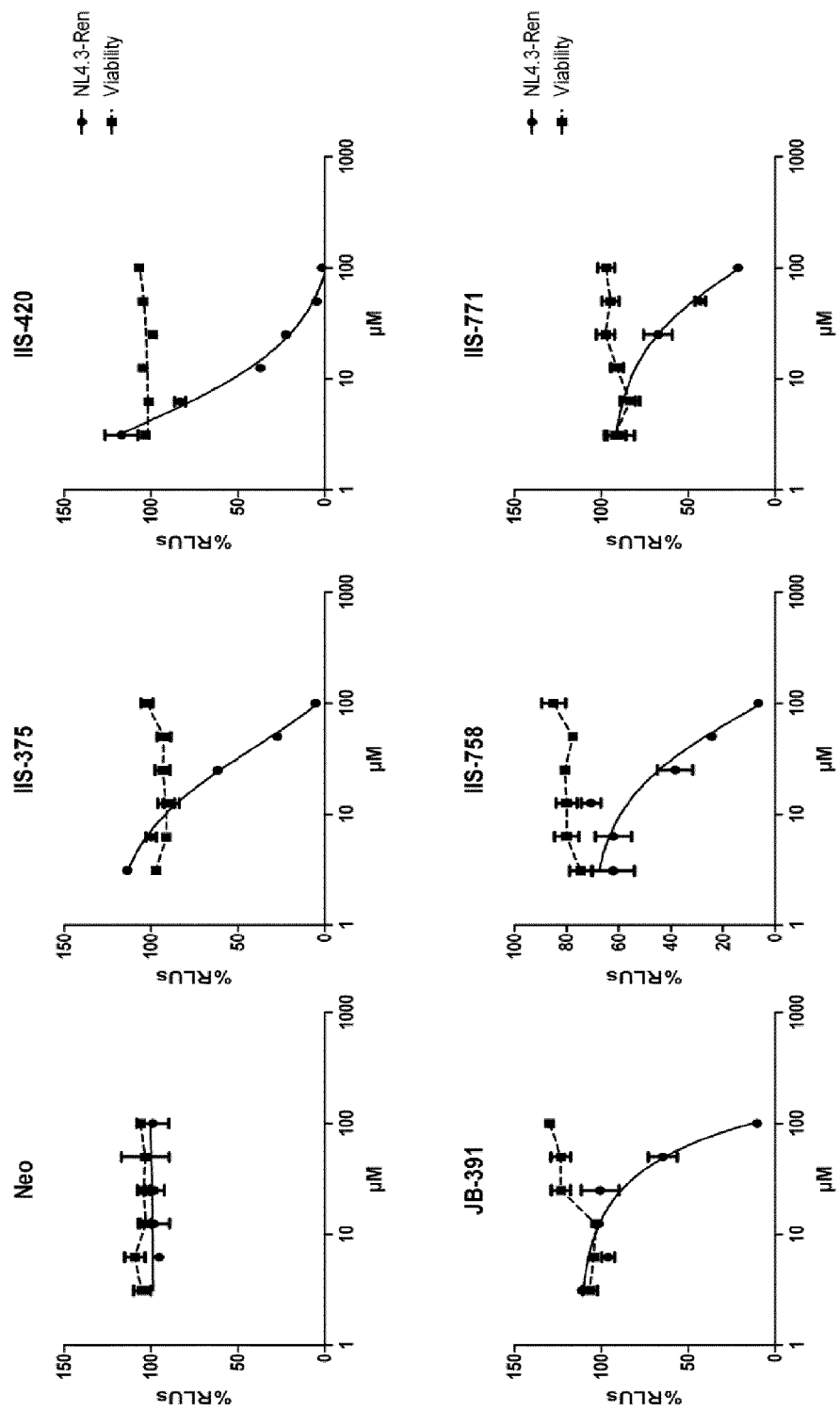
FIGS. 6a-d represent results of cellular assays. (a) Antiviral activity in HIV-1 infection assays (NL4.3-Ren) and cellular toxicity (viability) of terphenyl and biphenyl compounds and the reference antibiotic neomycin B. (b) Antiviral activity in HIV-1 transfection assays of terphenyl molecules. (c) Inhibition of Rev-mediated transport of RRE-containing RNA to the cytoplasm by the terphenyl IIS-420. (d) Inhibition of HIV-1 LTR-mediated transcription by terphenyls IIS-420, IIS-358 and IIS-758. In all cases, results are expressed as percentage of RLUs, where 100% are the luminescence levels obtained with the vehicle used to dissolve the compounds.

The terphenyls IIS-420, IIS-375, IIS-758, IIS-771, IIS-792 and IIS-806 inhibited HIV-1 replication with no cellular toxicity, as shown in Table 3a and FIG. 6a.

Table 3. Results of cellular assays. (a) Antiviral activity in HIV-1 infection assays ($EC_{50}$, NL4.3-Ren) and cellular toxicity ($CC_{50}$). (b) Antiviral activity in HIV-1 transfection assays ($EC_{50}$, post-integration). (c) Inhibition of Rev-mediated transport of RRE-containing RNA to the cytoplasm by the terphenyl IIS-420. In all cases, confidence intervals and $R^2$ values are shown when possible.

TABLE 3a

| compound | $EC_{50}$ (μM) (NL4.3-Ren) | $CC_{50}$ (μM) (celular viability) |
|---|---|---|
| Neomycin B | >100 | >100 |
| JB-391 | >50 < 100 | >100 |
| JB-398 | >100 | >100 |
| SC-30 | >50 < 100 | >100 |
| JB-399 | >100 | >100 |
| IIS-358 | >100 | >100 |
| IIS-311 | >100 | >100 |
| IIS-478 | >100 | >100 |
| IIS-530 | >100 | >100 |
| IIS-792 | 46.3 | >100 |
| Conf. int. 95% | 35.0-61.2 | |
| $R^2$ | 0.7029 | |
| IIS-758 | 32.3 | >100 |
| Conf. int. 95% | 20.6-50.5 | |
| $R^2$ | 0.7704 | |
| IIS-806 | 64.1 | >100 |
| Conf. int. 95% | 49.2-83.5 | |
| $R^2$ | 0.7861 | |
| IIS-771 | 42.6 | >100 |
| Conf. int. 95% | 32.3-56.1 | |
| $R^2$ | 0.8583 | |
| IIS-420 | 3.4 | >100 |
| Conf. int.. 95% | 1.7-6.9 | |
| $R^2$ | 0.9712 | |
| IIS-375 | 24.8 | >100 |
| Conf. int. 95% | 18.7-32.8 | |
| $R^2$ | 0.8928 | |

TABLE 3b

| Compound | IIS-420 | IIS-375 | IIS-758 | IIS-771 | JB-391 |
|---|---|---|---|---|---|
| $EC_{50}$ post-integration (μM) | 5.0 | 21.4 | 17.0 | >100 | >100 |
| Conf. Int. 95% | 0.7–34.0 | 15.3–29.9 | 3.6–80.7 | | |
| $R^2$ | 0.8648 | 0.9931 | 0.8629 | | |

TABLE 3c

| pCMV-Rev (ng)[a] | $IC_{50}$ (IIS-420, RRE-Rev) (μM) |
|---|---|
| 500 | >50 < 100 |
| 200 | 21.4 ± 6.3 |
| 20 | 10.4 ± 2.4 |

[a]These experiments were performed with a constant concentration of pDM628 (500 ng/well) and decreasing concentrations of pCMV-Rev IIS-420 was the most potent HIV-1 inhibitor, with an $EC_{50}$ value of 3.4 μM (Table 3a). As observed in the RRE-Rev$_{34-50}$ inhibition experiments in vitro, the compounds containing hydrophobic groups (methyl or ethyl) in the central benzene ring were also the most active compounds in vivo. The remaining ligands and neomycin B were not active or exhibited much weaker activities at the assay concentrations. None of the compounds showed cellular toxicity at concentrations below 100 μM (Table 3a and FIG. 6a).

Figure 6B:
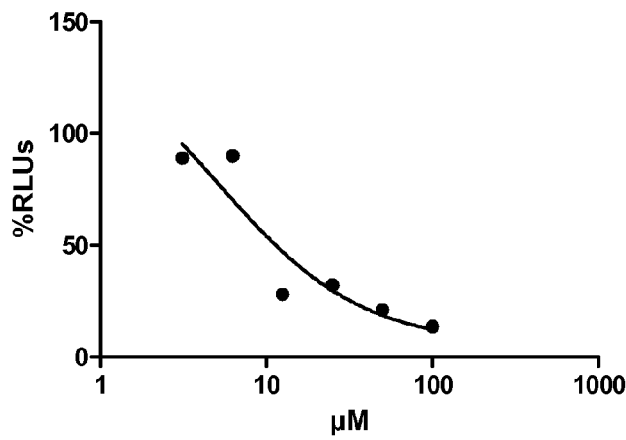
Figure 6B:
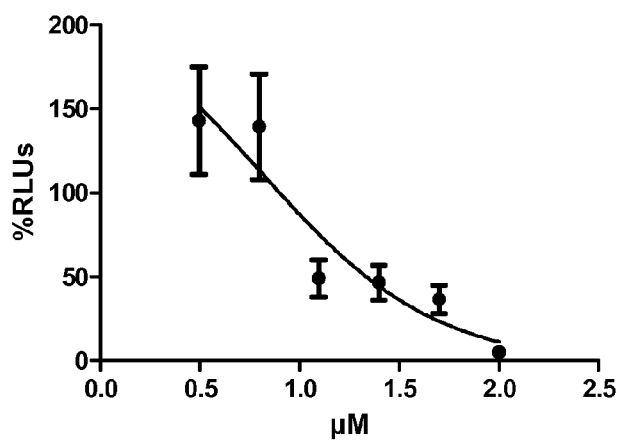
Figure 6B:
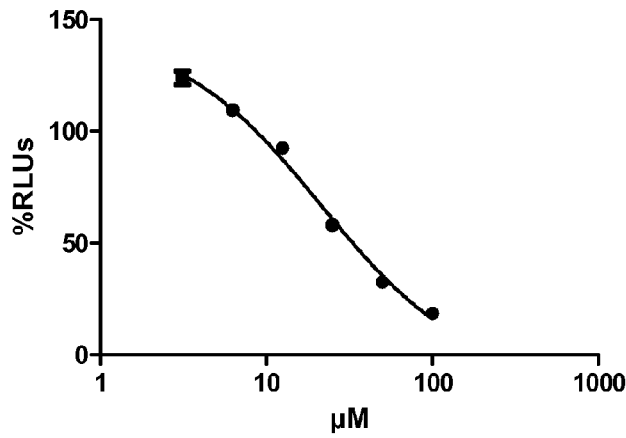

In order to evaluate the activity of the compounds in post-integration steps of the virus life cycle, we carried out an assay based on transfecting a full-length competent HIV-1 clone, where early steps of infection are bypassed and only post-integration events of the virus cycle occur. IIS-420, with an $EC_{50}$ value of 5.0 μM, was the most potent compound in this assay, followed by IIS-758 and IIS-375 (Table 3b and FIG. 6b). The $EC_{50}$'s of these terphenyls were similar to those obtained with the infection experiment (Table 3a), indicating that their main target was contained in transcriptional or post-transcriptional steps of the virus infectious cycle, as is the case for the RRE-Rev system.

5. The Bilaterally-Substituted Terphenyl IIS-420 Inhibits the RRE-Rev System Ex Vivo.

Figure 6C:
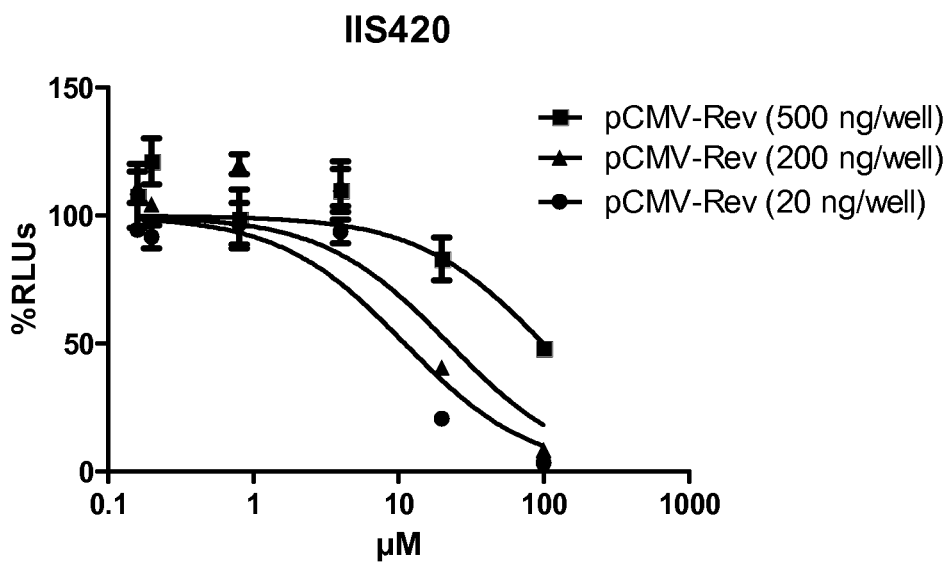

An assay based on transfecting plasmids encoding Rev and an RRE-luciferase reporter system was carried out. The results indicated that IIS-420 inhibited Rev-mediated transport of RRE-containing RNA from the nucleus to the cytoplasm. The $IC_{50}$ values ranged between 10.4 and 21.4 □M and depended on the concentration of Rev-encoding plasmid used in the assay (Table 3c and FIG. 6c). This result clearly establishes cellular inhibition of RRE-Rev ribonucleoprotein function.

6. Bilaterally-Substituted Terphenyls Inhibit Transcription Mediated by the HIV-1 LTR Promoter.

Figure 6D:
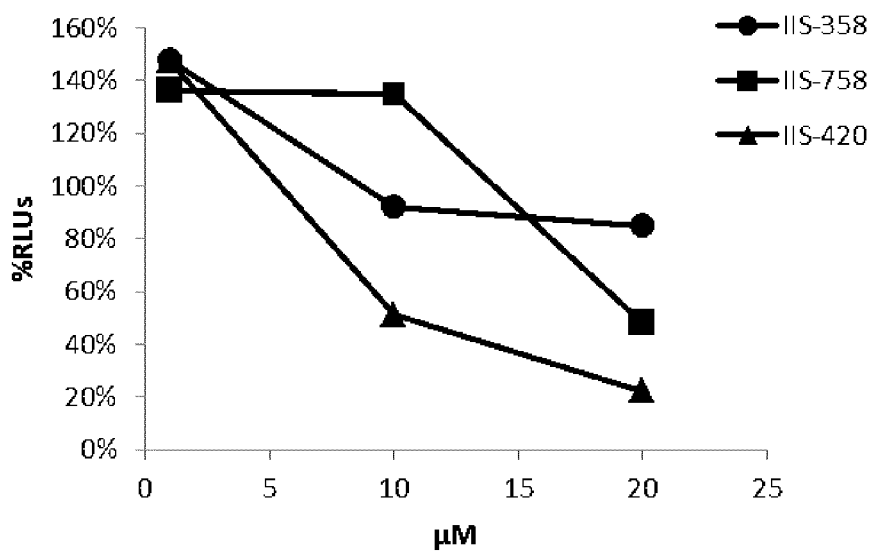

An assay based on transfecting an LTR-Luc plasmid(26) was performed to evaluate whether the terphenyls inhibited transcription mediated by the HIV-1 long terminal repeat (LTR) promoter. The terphenyls IIS-358, IIS-758 and IIS-420 inhibited transcription of the reporter gene (FIG. 6d).

Although the available data are consistent with an antiviral effect based on RRE-Rev inhibition, these results show that bilaterally-substituted terphenyls also inhibit transcription controlled by the HIV-1 LTR promoter.

7. Bilaterally-Substituted Terphenyls Exhibit Antibiotic Activity.

The antibiotic activity of selected biphenyl and terphenyl compounds was performed using a conventional disk diffusion assay(27). The observed disk susceptibilities indicated that the bilaterally-substituted terphenyl IIS-420 had weak but significant activity against both gram-negative (*Escherichia coli*) and gram-positive (*Staphilococcus aureus*) bacteria. In contrast, the biphenyls JB-391 and SC-30 and the 2'-methoxy terphenyls IIS-358 and IIS-478 were inactive (Table 4). This result shows that the bilaterally-substituted compounds of the invention can be used as new antibacterial agents.

TABLE 4

Comparative disk susceptibility of *E. coli* and *S. aureus* to five antibiotics, the biphenyls JB-391 and SC-30, and the terphenyls IIS-478, IIS-358 and IIS-420.

| Compound[a] | *E. coli*[b,c] | *S. aureus*[b,c] |
|---|---|---|
| Ampicillin | 25.6 ± 1.7 | 38.1 ± 1.6 |
| Tobramycin | 18.8 ± 2.2 | 17.6 ± 0.8 |
| Kanamycin A | 22.0 ± 2.0 | 16.5 ± 1.1 |
| Kanamycin B | 20.0 ± 2.1 | 16.7 ± 1.2 |
| Neomycin B | 15.2 ± 2.1 | 12.8 ± 1.9 |
| IIS-420 | 9.3 ± 0.4 | 9.8 ± 0.4 |

[a]The disk potencies were 20 μg of compound in all cases.
[b]The values represent the average and standard deviation of 2-10 independent experiments.
[c]JB-391, SC-30, IIS-478 and IIS-358 were inactive in this assay.

Obtaining the Pharmaceutical Compositions of the Present Invention

The pharmaceutical compositions of the present invention are prepared in a manner known per se, for example by means of conventional mixing, granulating, coating, dissolving, emulsifying or lyophilizing processes. Optionally, the manufacture of the compositions according to the present invention includes more steps such as liposomal encapsulation.

In particular, a tablet may be made by compression and molding, optionally with one or more accessory ingredients. Compressed tablets may be prepared by compressing in a suitable machine the active compound of the present invention in a free-flowing form, e.g., a powder or granules, optionally mixed with ingredients, such as, binders, lubricants, inert diluents, surface active or dispersing agents. Molded tablets may be made by molding in a suitable machine, a mixture of the powdered active compound with any suitable carrier.

In particular, a syrup or suspension may be made by adding the active compound of the present invention to a concentrated, aqueous solution of a sugar, e.g. sucrose, to which also any accessory ingredient may be added. Such accessory ingredients may include, flavoring, an agent to retard crystallization of the sugar or an agent to increase the solubility of any other ingredient, e.g., as a polyhydric alcohol, for example, glycerol or sorbitol.

Formulations for rectal administration may be made with a conventional carrier, e.g., cocoa butter or Witepsol S55 (commercial registered trademark). Specific details related to particular aspects of conventional processes of galenic development can be found in Swarbrick and Boylan's "Encyclopedia of pharmaceutical technology" (1988-2001 NY, Published by M. Dekker).

Alternatively, the compounds of the present invention may be made in liposomes or microspheres (or microparticles), such methods essentially comprising dissolving the compounds of the present invention in an aqueous solution, the appropriate phospholipids and lipids added, along with surfactants if required, and the material dialyzed or sonicated, as necessary. Liposomal encapsulation techniques are detailed in Claudio Nastruzzi's book "Liposheres in drug targets and delivery: approaches, methods, and applications" (Boca Raton 2005, published by CRC Press) and in Lasic and Papahadjopoulos' "Liposheres in drug targets and delivery: approaches, methods, and applications" (1998 Amsterdam, N.Y., Published by Elsevier).

EXAMPLES

The invention will now be further described by the following working examples, which are preferred embodiments of the invention. These examples are illustrative rather than limiting and it is to be understood that there may be other embodiments that fall within the spirit and scope of the invention as defined by the claims appended hereto.

Example 1

Structure-Based Design of RRE-Rev Inhibitors

The conformational analysis of an hexa-substituted terphenyl molecule was carried out using the Merck MMFF94s force field(28) within the MOE software package (CCG Inc.). We systematically varied the two benzene-benzene torsions by 30° intervals and minimized the potential energy of the conformers. Biphenyl and terphenyl molecules containing different substitution patterns were docked into the 1ETF RRE structure(7) using the Dock 5.0 algorithm(29).

In order to obtain an improved model of RRE-terphenyl complexes, subsequent docking calculations were carried out using the Autodock 3.05(30) and Gold 5.0(31) programs, guided by restraints based on intermolecular NOEs observed by NMR spectroscopy. Based on the NMR data (FIG. 3), the binding site of the ligands was defined around nucleotide C20. An illustrative example of these calculations is shown in FIG. 4.

Example 2

Preparation of RNA and Peptide Samples

The RRE RNA (SEQ ID No. 1) used in NMR spectroscopy and fluorescence polarization (FP) experiments was purchased from Dharmacon (Thermo Fisher Scientific Inc.), 2'-ACE de-protected, and purified following a procedure based on gel electrophoresis and dialysis. For the SPR experiments, 5'-biotin-RRE and two control 5'-biotin-RRE$_c$ (SEQ ID No: 2) and 5'-biotin-TAR$_c$ RNAs (SEQ ID No. 3) were purchased HPLC-purified from Microsynth AG and microdialyzed in HBS-EP buffer (10 mM HEPES pH 7.4, 150 mM NaCl, 3 mM EDTA and 0.005% (v/v) surfactant P20) prior to immobilization.

For the fluorescence polarisation experiments (FP), we used the peptide FITC-Ahx-GTRQARRNRRRRWRER-QRAAAAR-amide (SEQ ID No. 5; identified as frevp), containing an FITC fluorophore bound to the N-terminal glycine (Genscript Inc.). This peptide contains the Arg-rich Rev$_{34-50}$ residue tract forming the RNA-binding α-helix of Rev(21). For benchmarking the FP and SPR experiments, a similar but unlabeled succynyl-TRQARRNRRRRWRER-QRAAAAR-amide peptide (SEQ ID No. 4; identified as revp) was also purchased from Genscript Inc. Both peptides contain additional AAAAR amino acids at their C termini, shown to favour the α-helical conformation(22).

Example 3

SPR Experiments

The Surface Plasmon Resonance (SPR) experiments were carried out at 25° C. with a Biacore T100 optical biosensor system, 4-channel streptavidin-derivatized Series S SA chips, and either 10 mM MES (pH 6.25), 150 mM NaCl, 1 mM EDTA and 0.005% P20 or 10 mM HEPES pH 7.4, 150 mM NaCl, 3 mM EDTA and 0.005% P20 aqueous solutions as mobile phases. After immobilizing approximately 300 response units (RU) of the RRE, RRE$_c$ and TAR$_c$ RNA hairpins on the chips, the compounds were injected during 10-minute periods at a flow rate of 20 μL/min and at concentrations generally ranging from 0.01 μM to 100.0 μM, and then allowed to dissociate for 10 more minutes. The RNA surfaces were regenerated with solutions containing 0.5 to 1 M NaCl and 10 to 100 mM NaOH, depending on the ligand.

RNA-ligand SPR equilibrium dissociation constants ($K_d$) were determined by fitting the sensorgrams to one-site or two-site equations:

$$RU = \frac{RU_{max} \cdot C}{1 + K_d \cdot C} + RI$$

$$RU = \frac{RU_{max1} \cdot C}{1 + K_{d1} \cdot C} + \frac{RU_{max2} \cdot C}{1 + K_{d2} \cdot C} + RI$$

where RU is the response in the steady-state region of the sensorgrams, C is the concentration of free compound in equilibrium with the complex, $RU_{max}$ is the maximum response and RI is an offset term accounting for the bulk refractive index contribution of the sample. In these models, $K_d$, $RU_{max}$ and RI are adjustable parameters, and the stoichiometry of each binding site was determined by comparing the fitted $RU_{max}$ values with the predicted ones, calculated from the molecular weights of RNA and compound and the amount of RNA in the flow cell(32). The two-site equation was only utilized if it provided a clear curve-fitting improvement over the one-site model. The specificity of the RRE interaction was quantified by calculating the $K_d(RRE_c)/K_d(RRE)$ and $K_d(RRE)/K_d(TAR_c)$ ratios. All SPR experiments were double-referenced(33). Results are shown in Table 1 and FIG. 2.

Example 4

NMR Spectroscopy

NMR spectra were acquired in temperature-calibrated Bruker Avance 500 MHz and cryoprobe-equipped Bruker Avance 600 MHz spectrometers, and analysed using Topspin 1.3 (Bruker Biospin) and Sparky 3.110(34). The RRE samples used in ligand-binding NMR experiments were previously microdialyzed in an aqueous solution containing 10 mM sodium phosphate (pH 6.0) and 0.1 mM EDTA. The interaction of these RRE samples with biphenyl and terphenyl compounds was monitored using two-dimensional TOCSY experiments recorded in D$_2$O. Starting from free RRE, the RNA was progressively titrated with ligand until RNA:ligand molar ratios ranging from 1:2 to 1:6, depending on the observed spectral changes. The interaction between RRE and the reference antibiotic neomycin B was also monitored using a similar approach. Results are shown in FIG. 3.

The complexes of RRE with the best ligands (IIS-420, IIS-375 and IIS-806) were studied using a higher concentration of RNA (0.12 mM) and 1:1 to 1:4 RNA:terphenyl molar ratios. These systems were additionally studied using series of dqf-COSY, TOCSY and NOESY (with 100-800 ms mixing times), all with recycle delays of 2 seconds, as well as 1 D saturation transfer difference experiments. All of these experiments were recorded in $D_2O$ at several temperatures (between 2 and 46° C.).

Example 5

Fluorescence Polarization Experiments

The capacity of biphenyl and terphenyl ligands to inhibit the RRE-Rev$_{34-50}$ interaction in vitro was evaluated with a displacement assay based on fluorescence anisotropy. These experiments were conducted at 25° C. using 96-well plates and a Victor X5 (PerkinElmer Inc.) plate reader set up with 480 and 535 nm excitation and emission filters, respectively. The buffer used for these assays contained 30 mM HEPES (pH 6.8), 100 mM KCl, 10 mM sodium phosphate, 10 mM ammonium acetate, 10 mM guanidinium chloride, 2 mM $MgCl_2$, 20 mM NaCl, 0.5 mM EDTA and 0.001% (v/v) Triton X-100(35).

The RRE hairpin (SEQ. ID No 1; at a concentration of 2 or 60 nM) and frevp (SEQ ID. No. 5; 10 nM) were incubated with increasing amounts of compounds for 5 minutes. Anisotropy data were subsequently collected for 15 minutes at 5 minute intervals to ensure that full equilibration had been reached. $IC_{50}$ values were calculated by fitting observed anisotropy ($A_{obs}$) to the following equation with GraphPad Prism (GraphPad Software Inc.):

$$A_{obs} = A_f + \frac{(A_b - A_f)}{1 + \left(\frac{[I]}{IC_{50}}\right)^m}$$

where $A_f$ and $A_b$ are the anisotropy values measured for free and RRE-bound frevp, respectively, [I] is the total concentration of inhibitor, $IC_{50}$ is the 50% inhibitory concentration, and m is the slope of the linear portion of the sigmoidal curve.

Inhibition constants ($K_i$) were calculated from the $IC_{50}$ values using the following equation:

$$\log(IC_{50}) = \log\left(10^{\log(K_i)} \cdot \left(1 + \frac{[L]_t}{K_d}\right)\right)$$

where $[L]_t$ is the total concentration of frevp (10 nM) and $K_d$ is the RRE-frevp dissociation constant, 4.6±1.3 nM. This value was obtained from fitting with GraphPad Prism two direct RRE-frevp binding experiments where A was measured as a function of RRE concentration at a fixed 10 nM frevp concentration. The FP results are shown in FIG. 5 and Table 2.

Example 6

Plasmids, Viruses and Cells

Plasmids pNL4.3-Luc and pNL4.3 Ren were generated by cloning the luciferase and renilla genes, respectively, in the nef region of the proviral clone pNL4.3(36, 37). pCMV-Rev expresses Rev, and pDM628 is a Rev-dependent luciferase-based reporter plasmid in which the RRE and a luciferase-coding sequence have been cloned. In the LTR-Luc plasmid, the expression of the luciferase reporter depends on the HIV-1 LTR promoter(26).

MT-2 cells (American Type Culture Collection, Rockville, Md.) were cultured in RPMI 1640 medium containing 10% (v/v) fetal bovine serum, 2 mM I-glutamine, penicillin (50 IU/ml) and streptomycin (50 µg/ml) (all Whittaker M.A. Bio-Products). The cells were cultured at 37° C. in a 5% $CO_2$ humidified atmosphere and split twice a week.

Example 7

Cellular Assays

Evaluation of Anti-HIV-1 Activity. Infectious supernatants were obtained from calcium phosphate transfection on 293T cells of plasmids pNL4.3-Luc or pNL4.3-Ren. These supernatants were used to infect cells in the presence of the compounds to evaluate. Anti-HIV activity quantification was performed 48 h post-infection. Briefly, cells were lysed with 100 µl of buffer provided by "Luciferase Assay System Kit with Reporter Lysis Buffer" (Promega, Madison, Wis.). Relative luminescence units (RLUs) were obtained in a luminometer (Berthold Detection Systems, Pforzheim, Germany) after the addition of substrate to cell extracts. Cellular viability was evaluated with cells similarly treated with the same concentrations of compound. After 48 h, viability was evaluated with the CellTiter Glo (Promega) assay system following the Manufacturer's specifications. Inhibitory concentrations 50 ($EC_{50}$) and cytotoxic concentrations 50% ($CC_{50}$) were calculated using the GraphPad Prism software. The results are shown in Table 3a and FIG. 6a.

Transfection Assays. MT-2 cells were maintained in culture without stimuli and prior to assay cells were resuspended in 350 µl of RPMI without serum and antibiotics and transfected/pulsed at 320 V, 1500 µF and maximum resistance with the plasmids at a concentration of 0.5 µg/$10^6$ cells using an Easyject plus Electroporator (Equibio, Middlesex, UK). After transfection, cells were immediately cultured in RPMI with 10% fetal calf serum, glutamine and antibiotics, treated or not with different concentrations of compound and harvested 48 h later Luciferase activity (RLUs) was measured in a luminometer.

In the assays evaluating post-integration activity and LTR-dependent transcription, a full-length competent HIV-1 clone or an LTR-Luc plasmid, respectively, were transfected in the presence of compounds. RRE-Rev inhibition was analysed by transfecting pCMV-Rev and pDM628 plasmids. Transcripts produced upon transcription of pDM628 consisted in fragments encoding the luciferase gene and the RRE, where both elements were situated between a splicing donor and a splicing acceptor. In the presence of Rev, the RRE-Rev interaction enables export of the transcript to the cytoplasm, resulting in luciferase expression. The results of transfection assays are shown in Tables 3b and 3c and FIGS. 6b, 6c and 6d.

Example 8

Evaluation of Antibiotic Activity

Antibacterial activity was measured according to the Kirby-Bauer method(27). *Escherichia coli* (ATCC 53868) or *Staphilococcus aureus* (ATCC 35556) cultures were uniformly spread on agar plates. Sterilized 8 mm discs were placed on the surface of the plates and impregnated with 20 μL of a 1 μg/μL compound solution. After incubation of the plates during 16-18 hours at 37° C., the diameter of the inhibition area around each disk was measured. The assay was benchmarked with the antibiotics ampicillin, tobramycin, kanamycin A, kanamycin B and neomycin B. The relative disk susceptibilities of *E. coli* and *S. aureus* to these agents were in good agreement with values reported in the literature (see e.g. (38)). The results are shown in Table 4.

Example 9

Synthesis of Bilaterally Substituted 1,4-Linked Tricyclic Compounds

Starting fragments 1 and 2 were determined to be the key building blocks to introduce the required amino substitution in the final molecules. Fragment 1 was prepared from commercially available 4-bromo-3,5-dimethylphenol (6). The phenolic group of 6 was alkylated with iodomethane and the resulting methyl ether was then oxidized. Carboxylic acid 8 was converted to methyl ester 9. Reduction of 9 with LiBH$_4$ (lithium borohydride), followed by treatment with NBS (N-bromosuccinimide) and then NaCN (sodium cyanide) produced fragment 1 in good yield (Scheme 2).

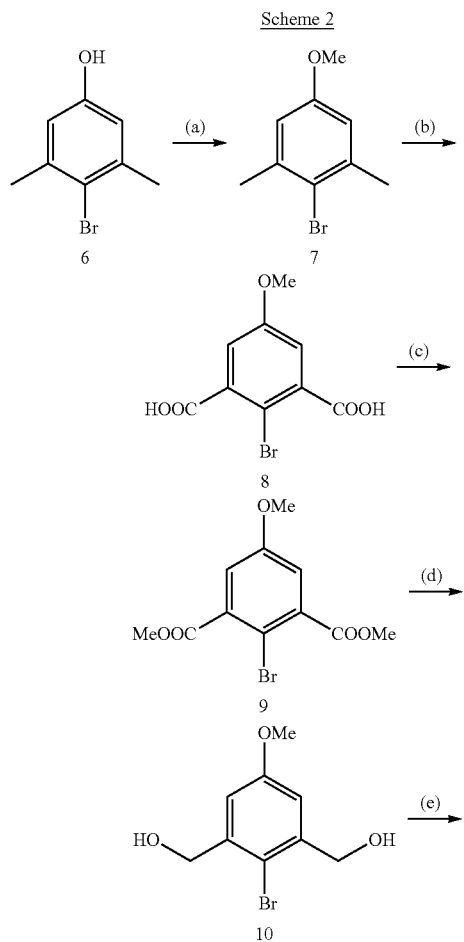

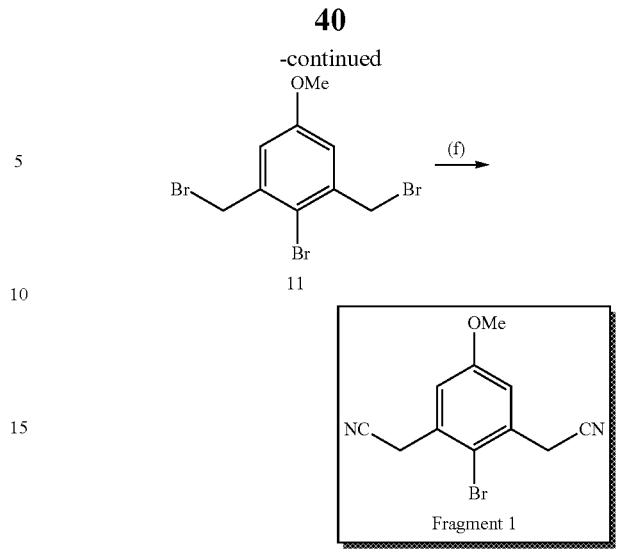

Reagents and conditions: (a) CH$_3$I, K$_2$CO$_3$, acetone, reflux, 12 h, quantitative; (b) KMnO$_4$, t-BuOH:H$_2$O, 100° C., 18 h, 68%; (c) MeOH, H$_2$SO$_4$, room temp, 12 h, 85%; (d) LiBH$_4$, THF, room temp, 12 h, 95%; (e) NBS, PPh$_3$, THF, room temp, 12 h, 85%; (f) NaCN, KI, 18-crown-6 ether, CH$_3$CN:H$_2$O, room temp, 24 h, 68%.

Synthesis of fragment 2 is shown in Scheme 3. Commercially available 12 was treated with formaldehyde to give alcohol 13. Compound 13 was converted to intermediates 14a-c by selective protection of its phenol group. Bromination of derivatives 14 and a subsequent nucleophilic substitution with NaCN provided 2 as a small library of O-protected bromophenol derivatives.

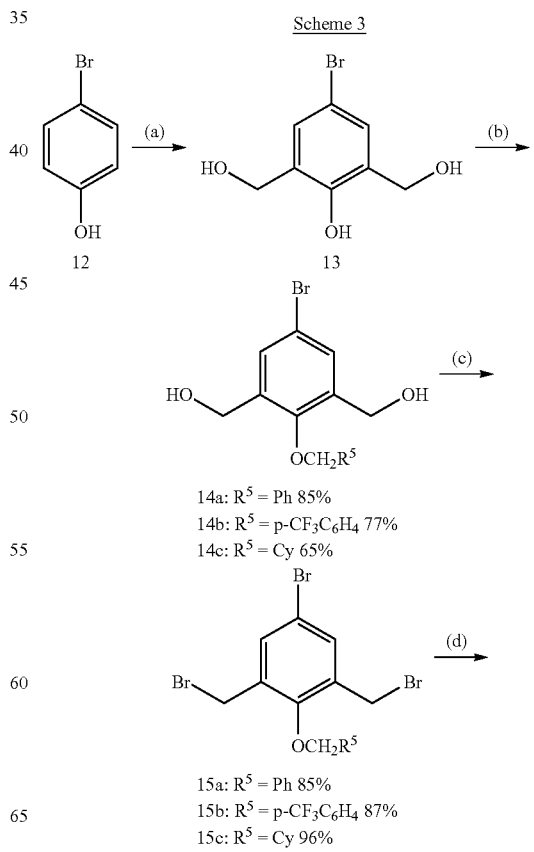

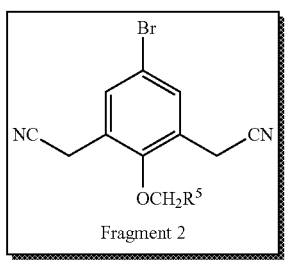

2a: R⁵ = Ph 60%
2b: R⁵ = p-CF₃C₆H₄ 57%
2c: R⁵ = Cy 54%

Reagents and conditions: (a) HCHO, aq NaOH 25%, 40° C., 48 h, 51%; (b) BrCH₂R⁵, K₃PO₄, acetone, room temp, 12 h; (c) NBS, PPh₃, THF, room temp, 24 h; (d) NaCN, KI, 18-crown-16 ether, CH₃CN:H₂O, room temp, 24 h.

As mentioned above, the synthetic route was based on sequential Suzuki cross-coupling reactions in which various aryl boronic esters were used as coupling partner. Boronic esters 3 were commercially available except for 3d and 3e.

Commercial available boronic esters

3a
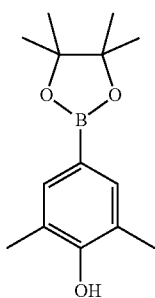

3b
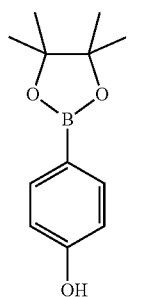

3c
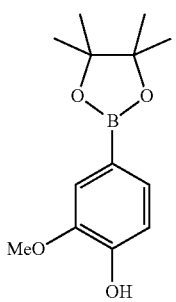

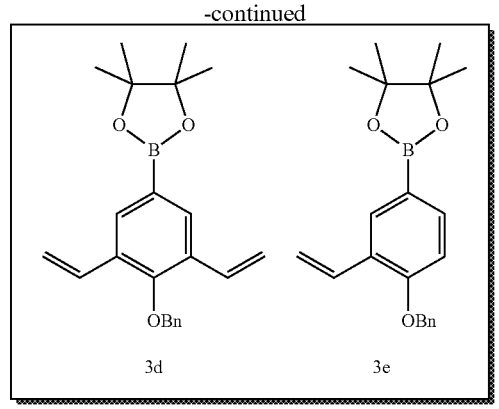

Vinyl derivatives 3d and 3e were synthesized as shown in Scheme 4. First, dialdehyde 16a was prepared from commercially available 4-bromophenol by a Duff's reaction. Both precursors 16a and 16b underwent the same synthetic pathway consisting of a protection of the phenol as benzyl group, a subsequent Wittig reaction with MePh₃PBr, and final boronic ester formation catalyzed by palladium under microwave irradiation.

Scheme 4

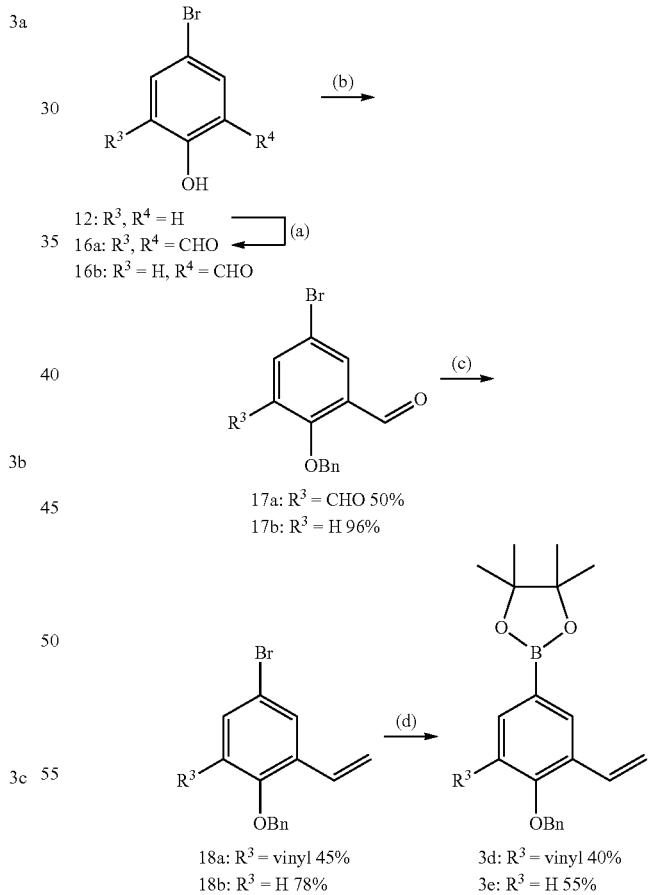

Reagents and conditions: (a) Duff's reaction, TFA, hexamethylenetetramine, 150° C., 48 h, 50%; (b) BrBn, K₃PO₄, acetone, reflux, 8 h; (c) MePh₃PBr, NaH, THF, 0° C., 16 h; (d) bis(pinacolate) diboron, KOAc, PdCl₂(dppf), dioxane, 30 min, 120° C. MW.

With all starting materials in hand, the complementary synthesis of biphenyl backbones combining fragments 1 and 2 (Scheme 5) was also envisioned. In this way, although a more complex terphenyl scaffold was aimed, the activity of biaryl structures was also evaluated.

Scheme 5

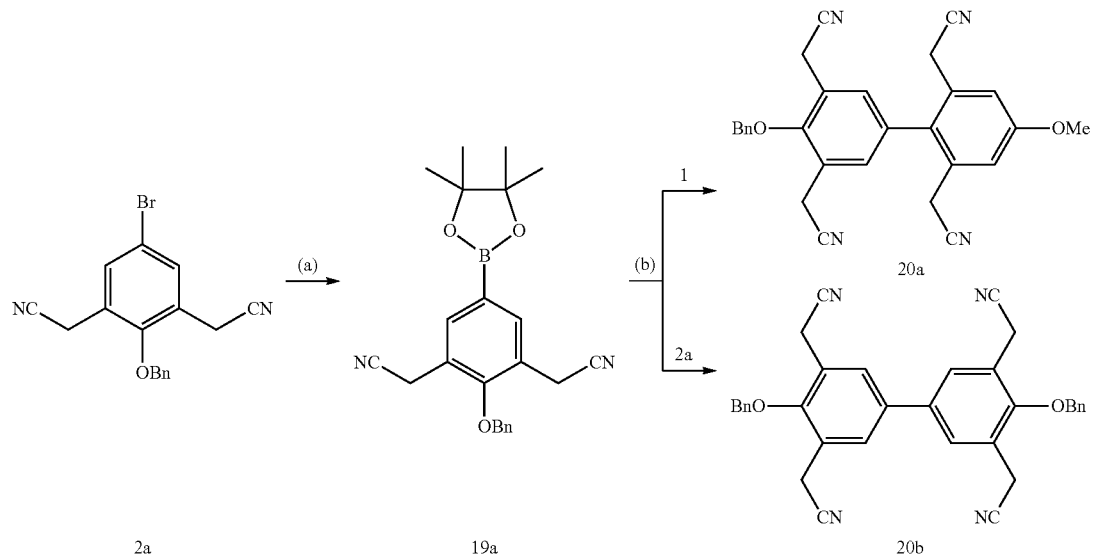

Reagents and conditions: (a) bis(pinacolate) diboron, KOAc, PdCl₂(dppf), DME, 30 min, 120° C. MW, 60%; (b) Pd(OAc)₂, PPh₃, K₃PO₄, DMSO, 1-2 h, 125° C. MW, 20a 42%, 20b 44%.

As shown in Scheme 5, a palladium-based cross-coupling reaction of 2a with bis(pinacolate)diboron afforded intermediate 19a. The resulting boronic ester 19a was coupled with synthons 1 and 2a to provide biphenyls 20a and 20b respectively. Pleasingly, it was observed that the homo-coupling reaction of 1 was also feasible involving a one-pot process in which the boronic partner was formed in situ (Scheme 6).

Scheme 6

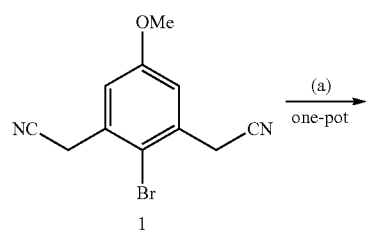

Reagents and conditions: (a) bis(pinacolate) diboron, K₃PO₄, PdCl₂(dppf), DME, 60 min, 120° C. MW, 84%.

Next step was the treatment of nitriles 20a-c with a borane tetrahydrofurane complex solution, and then HCl 4M in dioxane to give the ammonium salts 22a-b (Scheme 7). Benzyl protected derivatives 20a-b were additionally subjected to a previous hydrogenolysis to furnish alcohols 21a-b.

Scheme 7

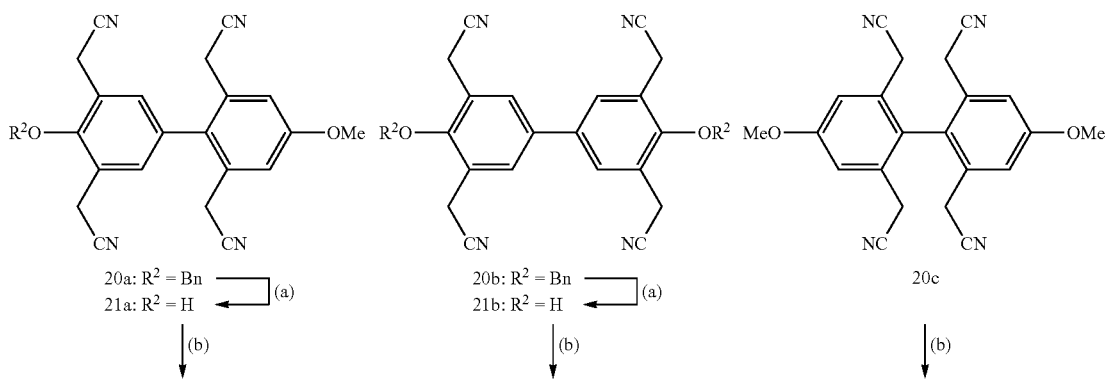

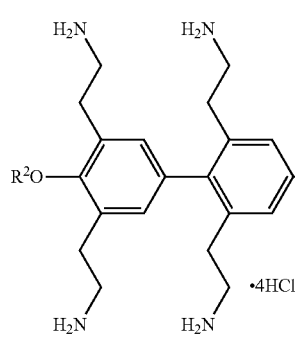

22a: R² = Bn 16%
22d: R² = H 15%

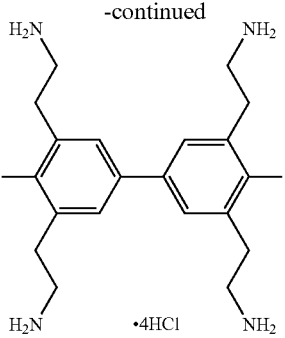

22b 12%

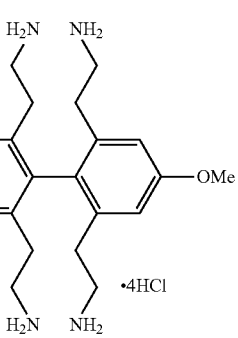

22c 40%

Reagents and conditions: (a) Pd/C (10 mol %), H₂ 1 atm, room temp, 2 h, quantitative; (b) BH₃, THF, reflux, 5 days then HCl 4M in dioxane.

Based on the synthetic approach used, the desired terphenyls 5 were synthesized as follows. Starting synthon 1 was subjected to a Suzuki cross-coupling reaction with aryl boronic esters 3a-e catalyzed by palladium under optimized conditions (Scheme 8). Removal of the benzyl group of 23d-e and subsequent triflation of the phenols 23a-c and 24a-b generated 25a-e in good yields. Before coupling triflates 25 with the corresponding boronic ester 2, the latter must be prepared separately as depicted in Scheme 9. Following the same procedure used before for 2a (R⁵=Ph), compounds 19b-d were synthesized by microwave-assisted Pd-catalyzed coupling reaction with bis(pinacolate)diboron.

Scheme 8

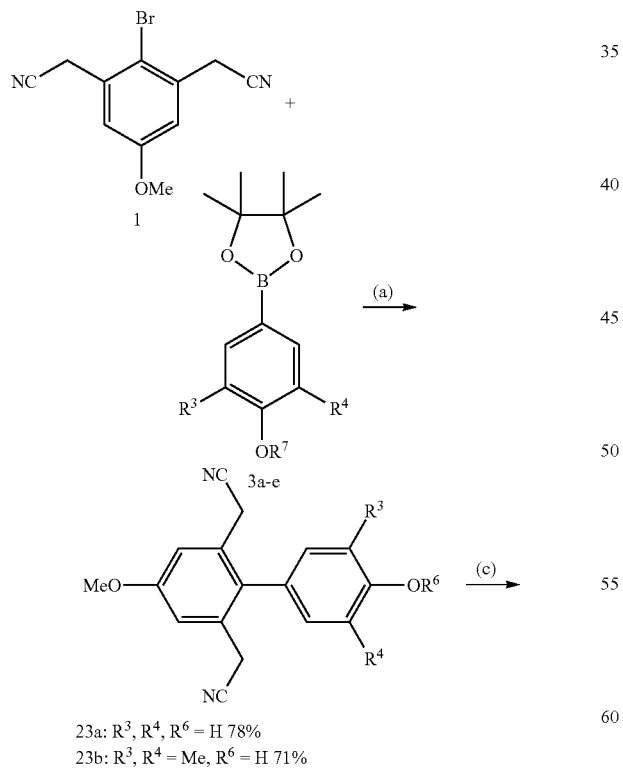

23a: R³, R⁴, R⁶ = H 78%
23b: R³, R⁴ = Me, R⁶ = H 71%
23c: R³ = OMe, R⁴, R⁶ = H 80%
23d: R³ = vinyl, R⁴ = H, R⁶ = Bn 42%
24a: R³ = Et, R⁴ = H, R⁶ = H 93%
23e: R³, R⁴ = vinyl, R⁶ = Bn 30%
24b: R³, R⁴ = Et, R⁶ = H 95%

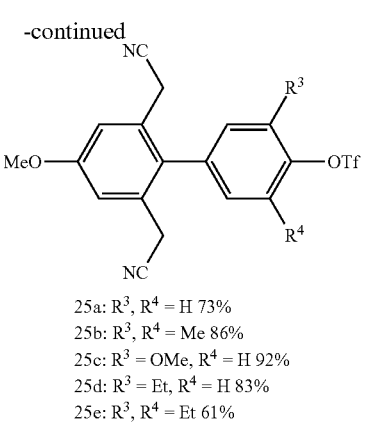

25a: R³, R⁴ = H 73%
25b: R³, R⁴ = Me 86%
25c: R³ = OMe, R⁴ = H 92%
25d: R³ = Et, R⁴ = H 83%
25e: R³, R⁴ = Et 61%

Reagents and conditions: (a) K₃PO₄, PdCl₂(dppf), CH₃CN:H₂O (7:3), 30 min, 120° C. MW; (b) H₂, Pd(OH)₂, EtOH, room temp, 12 h; (c) Tf₂O, pyridine, CH₂Cl₂, room temp, 2 h.

Scheme 9

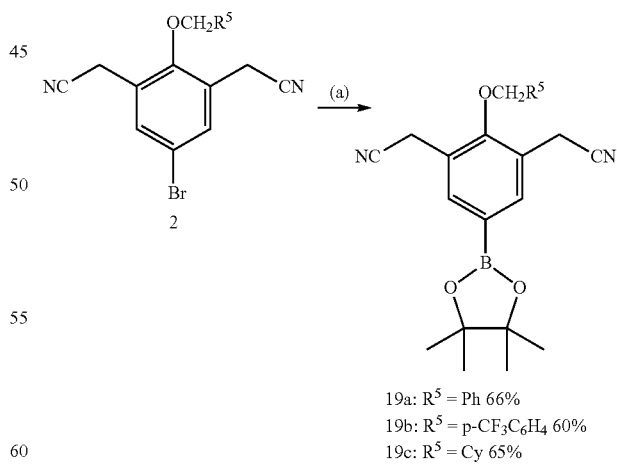

19a: R⁵ = Ph 66%
19b: R⁵ = p-CF₃C₆H₄ 60%
19c: R⁵ = Cy 65%

Reagents and conditions: (a) bis(pinacolate) diboron, KOAc, PdCl₂(dppf), dioxane, 30 min, 120° C. MW.

Next, the last Suzuki cross-coupling reaction was performed on triflates 25 and boronic esters 19 to afford the desired terphenyl derivatives 4a-g which were converted to the corresponding ammonium salt 5 by first reduction with BH$_3$/THF followed by treatment with HCl 4M in dioxane.

Scheme 10

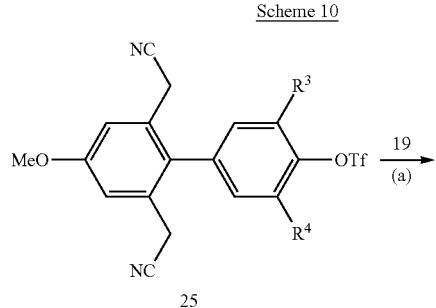

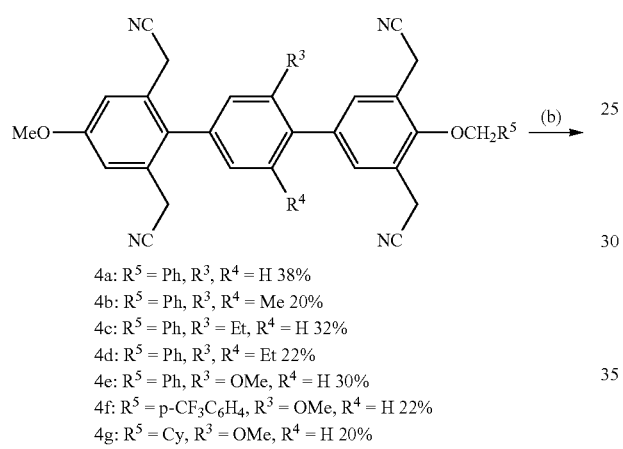

4a: R$^5$ = Ph, R$^3$, R$^4$ = H 38%
4b: R$^5$ = Ph, R$^3$, R$^4$ = Me 20%
4c: R$^5$ = Ph, R$^3$ = Et, R$^4$ = H 32%
4d: R$^5$ = Ph, R$^3$, R$^4$ = Et 22%
4e: R$^5$ = Ph, R$^3$ = OMe, R$^4$ = H 30%
4f: R$^5$ = p-CF$_3$C$_6$H$_4$, R$^3$ = OMe, R$^4$ = H 22%
4g: R$^5$ = Cy, R$^3$ = OMe, R$^4$ = H 20%

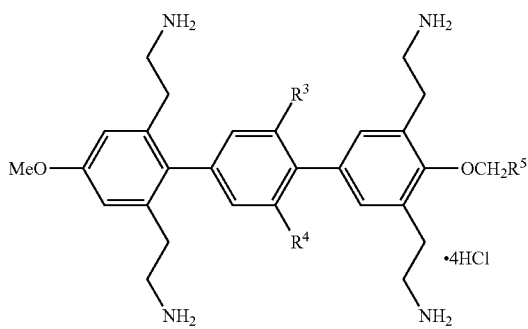

5a: R$^5$ = Ph, R$^3$, R$^4$ = H 30%
5b: R$^5$ = Ph, R$^3$, R$^4$ = Me 32%
5c: R$^5$ = Ph, R$^3$ = Et, R$^4$ = H 43%
5d: R$^5$ = Ph, R$^3$, R$^4$ = Et 20%
5e: R$^5$ = Ph, R$^3$ = OMe, R$^4$ = H 36%
5f: R$^5$ = p-CF$_3$C$_6$H$_4$, R$^3$ = OMe, R$^4$ = H 47%
5g: R$^5$ = Cy, R$^3$ = OMe, R$^4$ = H 42%

Reagents and conditions: (a) K$_3$PO$_4$, PdCl$_2$(dppf), CH$_3$CN:H$_2$O (7:3), 30 min, 120° C. MW; (b) BH$_3$, THF, reflux, 5 days then HCl 4M in dioxane.

Additionally, substrates 4a-e were debenzylated under standard conditions to give deprotected ammonium salts 5h-l quantitatively, as shown in Scheme 11. In this way, an assorted library of strategically functionalized bi- and terphenyl backbones was prepared.

Scheme 11

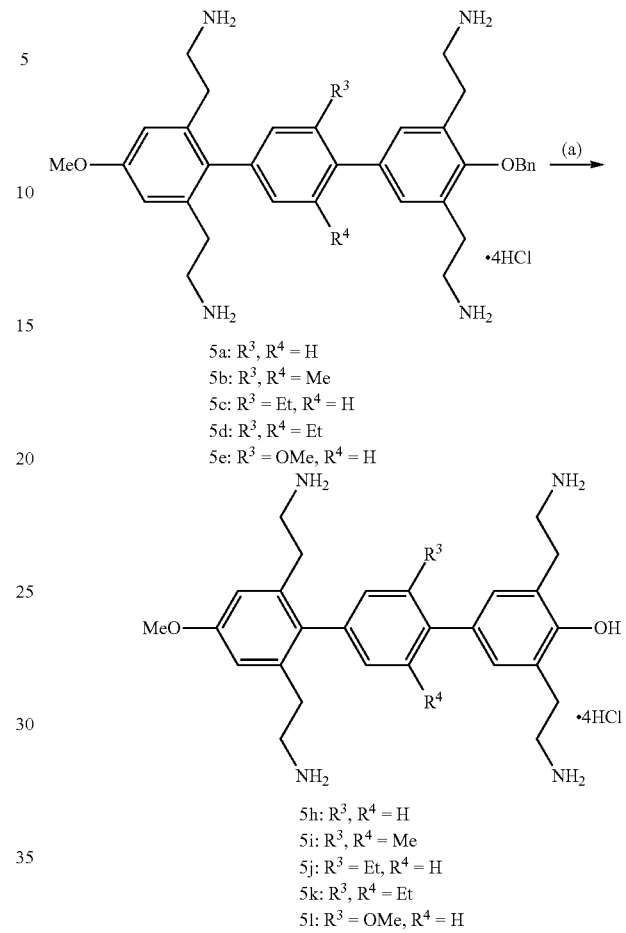

5a: R$^3$, R$^4$ = H
5b: R$^3$, R$^4$ = Me
5c: R$^3$ = Et, R$^4$ = H
5d: R$^3$, R$^4$ = Et
5e: R$^3$ = OMe, R$^4$ = H

5h: R$^3$, R$^4$ = H
5i: R$^3$, R$^4$ = Me
5j: R$^3$ = Et, R$^4$ = H
5k: R$^3$, R$^4$ = Et
5l: R$^3$ = OMe, R$^4$ = H

Reagents and conditions: (a) Pd/C (10 mol %), H$_2$ 1 atm, room temp, 2 h, quantitative.

Other bilaterally-substituted 1,4-linked tricyclic compounds containing rings different from benzene can be similarly prepared using sequential Suzuki-Myaura cross-coupling reactions. For example, the synthesis of 3,6-diphenyl-pirydazine compounds involves cross-couplings of commercially available 3,6-dichloropyridazine derivatives and aryl-boronic acids:

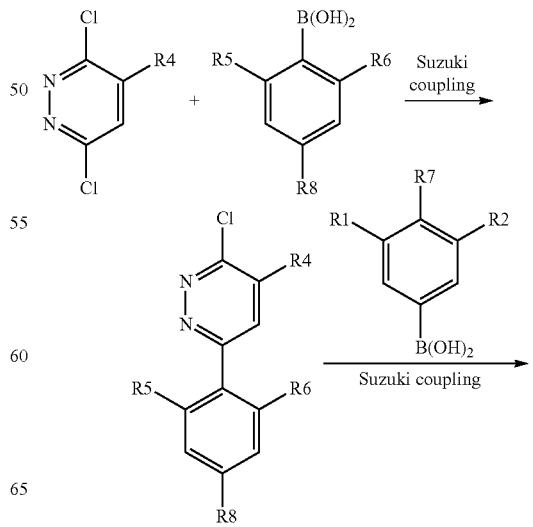

-continued

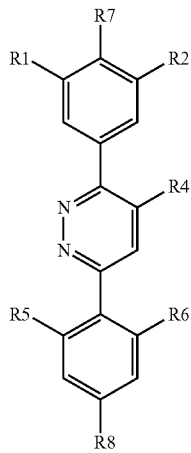

Preparation of Byphenyls 23 and 24

A mixture of corresponding boronic ester 3a-e (1.1 equiv.), aryl halide 1 (1 equiv.) and PdCl$_2$(dppf) (10% mol) was dissolved in MeCN:H$_2$O (7:3) (0.15 M) and K$_3$PO$_4$ (3 equiv.) was added. The mixture was heated at 120° C. in a microwave oven for 30 minutes. After cooling, the organic phase was decanted, washed with brine, dried over anhydrous Na$_2$SO$_4$, and concentrated under vacuum. The crude product was purified by flash chromatography on silica gel employing mixtures of n-hexane:EtOAc as eluents.

Benzyl Ether Hydrogenolysis to Obtain Phenols 24a-b

The mixture of the corresponding benzylated compound 23 (1 equiv.) and Pd(OH)$_2$ 20% wt (0.5 equiv.) in ethanol (0.1 M) was stirred under hydrogen atmosphere at 10 atm for 20 hours. The mixture was filtered and washed with EtOAc. The organic phase was evaporated to afford the product 24a-b without further purification.

Procedure for the Triflation Reaction

To a solution of the corresponding phenol 24 (1 equiv.) in anhydrous CH$_2$Cl$_2$ (0.2 M) was added pyridine (2.5 equiv.) and trifluoromethanesulfonic anhydride (1.2 equiv.) dropwise at 0° C. After complete addition, the mixture was warmed to room temperature and allowed to stir for 90 minutes. The mixture was then diluted with Et$_2$O, quenched with 10% aq. HCl and washed successively with saturated NaHCO$_3$, and brine. The organic phase was dried over anhydrous Na$_2$SO$_4$ and concentrated under vacuum to give a crude product, which was purified by column chromatography employing mixtures of n-hexane:EtOAc as eluents.

General Procedure for Terphenyl Synthesis

A mixture of corresponding boronic ester 19 (1.2 equiv.), triflate 25 (1 equiv.), K$_3$PO$_4$ (3 equiv.) and PdCl$_2$(dppf) (10% mol) was dissolved in MeCN:H$_2$O (7:3) (0.15 M). The mixture was heated at 120° C. in a microwave oven for 30 minutes. After cooling, the organic phase was decanted, washed with brine, dried over anhydrous Na$_2$SO$_4$, filtered, and concentrated under vacuum to give a crude product, which was purified by column chromatography employing mixtures of n-hexane:EtOAc as eluents.

General Procedure for Nitrile Reduction

Nitrile compound 4 (1 equiv.) was dissolved in anhydrous THF (0.05 M), then borane THF complex solution 1 M was added (12 equiv.) and the mixture was refluxed under N$_2$ atmosphere for 5 days. After that time, HCl 4 M in dioxane (16 equiv.) was added and the mixture was refluxed for 2 hours. The aqueous solution was washed several times with CH$_2$Cl$_2$ and then evaporated under vacuum. The recovered solid was dissolved in MeOH and precipitated by addition of Et$_2$O.

General Procedure for Benzyl Group Removal

The mixture of chlorhydrate 5a, 5b, 5c, 5d or 5e (1 equiv.) and Pd/C 10% wt (10% mol) in MeOH (0.03M) was stirred under H$_2$ atmosphere (1 atm) for 1 hour. The mixture was filtered and washed with MeOH. The combined organic phase was evaporated to afford the final product as a white solid. No further purification was needed.

2,2',2'',2'''-[4''-(Benzyloxy)-4-methoxy-3',5'-dimethyl-(1,1':4',1''-terphenyl)-2,3'',5'',6-tetrayl]tetraethanamine chlorhydrate (IIS-375) (5b)

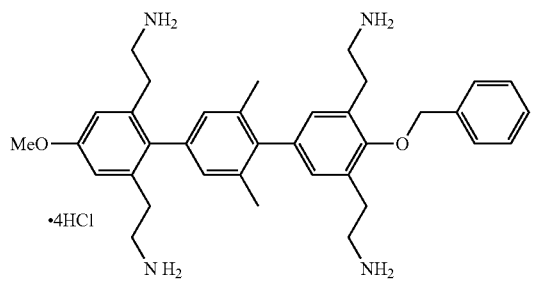

2,2',2'',2'''-[4''-(Benzyloxy)-4-methoxy-3',5'-dimethyl-(1,1':4',1''-terphenyl)-2,3'',5'',6-tetrayl]tetraethanamine chlorhydrate was synthesized following the method above starting from 4b. The crude product was obtained as a white solid (32% yield).

R$_f$: 0 (MeOH). $^1$H NMR (300 MHz, CDCl$_3$) δ=δ 7.60-7.32 (m, 5H), 7.02 (s, 2H), 6.93 (s, 2H), 6.83 (s, 2H), 4.99 (s, 2H), 3.84 (s, 3H), 3.08-2.92 (m, 8H), 2.84-2.82 (m, 4H), 2.71-2.62 (m, 4H), 2.09 (s, 6H). $^{13}$C NMR (75 MHz, CDCl$_3$) δ=δ 180.4, 160.4, 155.9, 141.4, 139.4, 139.3, 138.7, 137.5, 135.7, 133.7, 131.3, 130.1, 129.6, 129.3, 129.1, 129.1, 114.4, 77.0, 62.4, 55.8, 42.6, 42.4, 35.7, 32.6, 24.3, 21.2. HRMS (ESI) calcd. for C$_{36}$H$_{47}$N$_4$O$_2$ [M+H]$^+$: 567.3699. Found: 567.3653. Melting point: >300° C.

2,2',2'',2'''-[4''-(Benzyloxy)-3'-ethyl-4-methoxy-(1,1':4',1''-terphenyl)-2,3'',5'',6-tetrayl]tetraethanamine chlorhydrate (IIS-758) (5c)

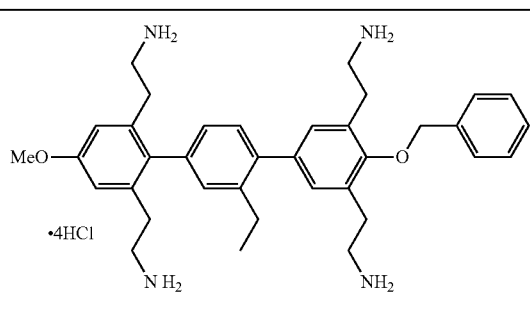

2,2',2",2'''-[4"-(Benzyloxy)-3'-ethyl-4-methoxy-(1,1':4',1"-terphenyl)-2,3",5",6-tetrayl]tetraethanamine chlorhydrate was synthesized following the method above starting from 4c. The crude product was obtained as a white solid (43% yield).

Rf: 0 (MeOH). $^1$H RMN (300 MHz, D$_2$O) δ=7.62-7.50 (m, 5H), 7.45 (d, J=7.7 Hz, 1H), 7.40 (s, 1H), 7.28 (s, 1H), 7.22-7.14 (m, 1H), 7.05 (s, 2H), 5.02 (s, 2H), 3.95 (s, 3H), 3.37-3.25 (m, J=7.3 Hz, 4H), 3.21-3.01 (m, J=16.2, 8.7 Hz, 8H), 2.93-2.79 (m, 4H), 2.72 (q, J=15.0, 7.5 Hz, 2H), 1.14 (t, J=7.5 Hz, 3H). $^{13}$C RMN (75 MHz, D$_2$O) δ=158.5, 153.9, 142.7, 139.6, 138.5, 137.8, 137.0, 136.0, 134.9, 130.8, 130.6, 130.4, 129.3, 129.2, 129.1, 127.3, 114.3, 76.6, 61.6, 55.7, 40.0, 39.8, 39.6, 31.4, 28.2, 28.0, 25.9, 15.3. HRMS (ESI) calcd. for C$_{36}$H$_{47}$N$_4$O$_2$[M+H]$^+$: 567.3699. Found: 567.3694. Melting point: 282-286° C.

2",3,5,6"-Tetrakis(2-aminoethyl)-4"-methoxy-2',6'-dimethyl-(1,1':4',1"-terphenyl)-4-ol chlorhydrate (IIS-420) (5i)

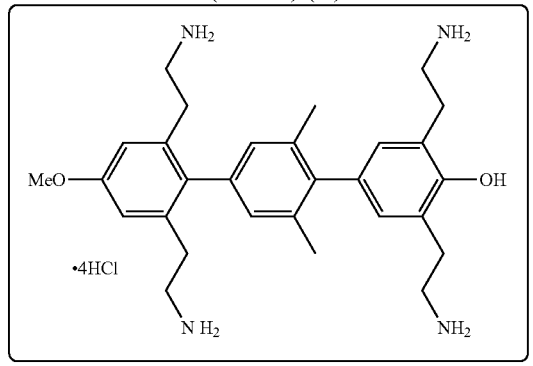

2",3,5,6"-Tetrakis(2-aminoethyl)-4"-methoxy-2',6'-dimethyl-(1,1':4',1"-terphenyl)-4-ol chlorhydrate was synthesized following the method above starting from 5b. The crude product was obtained as a white solid (99% yield).

Rf: 0 (MeOH). $^1$H NMR (300 MHz, MeOD) δ=δ 7.13 (s, 1H), 6.86 (s, 2H), 6.75 (d, J=3.8 Hz, 5H), 3.81 (s, 3H), 2.99 (d, J=5.8 Hz, 4H), 2.85 (d, J=5.8 Hz, 4H), 2.77-2.64 (m, 4H), 2.64-2.50 (m, 4H), 2.05 (s, 6H). $^{13}$C NMR (75 MHz, MeOD) δ=160.1, 155.9, 142.1, 140.1, 139.3, 137.6, 135.9, 132.1, 131.1, 130.1, 129.0, 128.4, 114.0, 66.9, 58.3, 55.7, 43.5, 42.8, 42.7, 37.6, 35.1, 21.3, 18.4, 15.4. HRMS (ESI) calcd. for C$_{29}$H$_{41}$N$_4$O$_2$ [M+H]$^+$: 478.3230. Found: 478.3169. Melting point: >300° C.

2",3,5,6"-Tetrakis(2-aminoethyl)-2',6'-diethyl-4"-methoxy-(1,1':4',1"-terphenyl)-4-ol chlorhydrate (IIS-806) (5k)

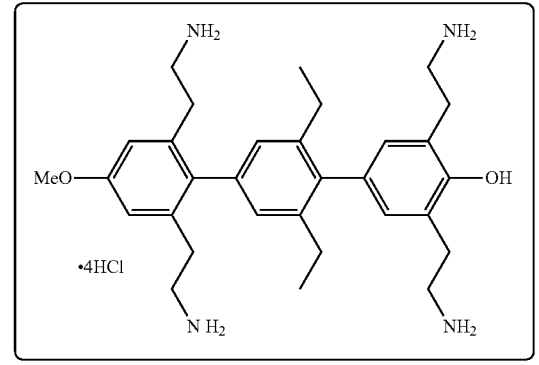

2",3,5,6"-Tetrakis(2-aminoethyl)-2',6'-diethyl-4"-methoxy-(1,1':4',1"-terphenyl)-4-ol chlorhydrate was synthesized following the method above starting from 5d. The crude product was obtained as a white solid (99% yield).

Rf: 0 (MeOH). $^1$H NMR (300 MHz, D$_2$O) δ=7.45 (d, J=7.7 Hz, 1H), 7.36-7.28 (m, 3H), 7.21 (d, J=7.7 Hz, 1H), 7.05 (s, 2H), 3.95 (s, 3H), 3.46-3.35 (m, 4H), 3.23-3.14 (m, 4H), 3.13-3.02 (m, 4H), 2.93-2.80 (m, 4H), 2.74 (q, J=7.5 Hz, 4H), 1.15 (t, J=7.5 Hz, 6H). $^{13}$C RMN (75 MHz, D$_2$O) δ=158.5, 151.3, 142.8, 139.8, 137.5, 137.0, 134.9, 130.7, 130.5, 130.4, 127.3, 125.7, 114.2, 61.6, 55.7, 49.0, 40.0, 39.6, 31.4, 28.2, 27.9, 25.8, 15.2. HRMS (ESI) calcd. for C$_{31}$H$_{45}$N$_4$O$_2$ [M+H]$^+$: 505.3543. Found: 505.3478. Melting point: >300° C.

2",3,5,6"-Tetrakis(2-aminoethyl)-2',4"-dimethoxy-(1,1':4',1"-terphenyl)-4-ol chlorhydrate (IIS-358) (5l)

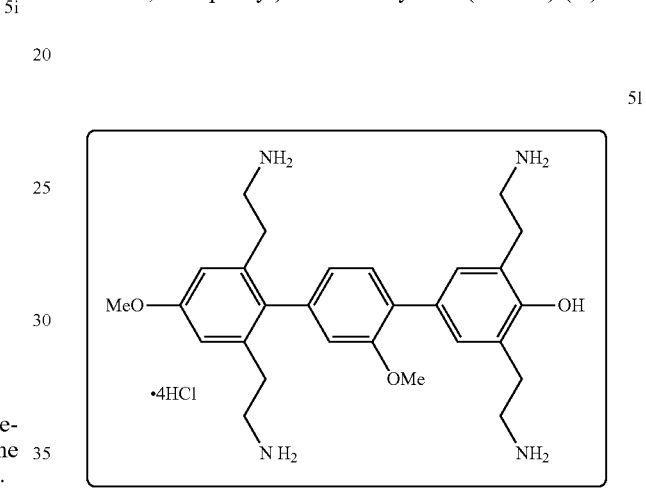

2",3,5,6"-Tetrakis(2-aminoethyl)-2',4"-dimethoxy-(1,1':4',1"-terphenyl)-4-ol chlorhydrate was synthesized following the method above starting from 5e. The crude product was obtained as a white solid (99% yield).

Rf: 0 (MeOH). $^1$H NMR (300 MHz, MeOD) δ=7.38-7.35 (m, 3H), 6.85-6.80 (m, 4H), 3.91 (s, 3H), 3.82 (s, 3H), 2.72-2.81 (m, 4H), 2.92-3.01 (m, 4H), 3.08-3.11 (m, 4H), 3.15-3.26 (m, 4H). $^{13}$C NMR (75 MHz, MeOD) δ=161.8, 157.8, 155.9, 142.9, 142.6, 134.8, 128.5, 128.4, 127.9, 124.0, 121.9, 121.0, 112.6, 111.4, 56.8, 56.0, 42.0, 34.9, 30.1. HRMS (ESI) calcd. for C$_{28}$H$_{39}$N$_4$O$_3$ [M+H]$^+$: 479.3022. Found: 479.2965. Melting point: >300° C.

REFERENCES

1. Richman D D, Margolis D M, Delaney M, Greene W C, Hazuda D, Pomerantz R J. The challenge of finding a cure for HIV infection. Science. 2009; 323(5919):1304-7.
2. Ward C J. New drugs for HIV-1: challenges and novel candidates. Expert Rev Anti Infect Ther. 2010; 8(10): 1093-5.
3. Sharp P A. The centrality of RNA. Cell. 2009; 136(4): 577-80.
4. Gallego J, Varani G. Targeting RNA with Small Molecule Drugs: Therapeutic Promise and Chemical Challenges. Acc Chem Res. 2001; 34:836-43.
5. Guan L, Disney M D. Recent advances in developing small molecules targeting RNA. ACS Chem Biol. 2012; 7(1):73-86.

6. Hermann T. Drugs targeting the ribosome. Curr Opin Struct Biol. 2005; 15(3):355-66.
7. Battiste J L, Mao H, Rao N S, Tan R, Muhandiram D R, Kay L E, et al. a Helix-RNA Major Groove Recognition in an HIV-1 Rev Peptide-RRE RNA Complex. Science. 1996; 273:1547-51.
8. Daugherty M D, Liu B, Frankel A D. Structural basis for cooperative RNA binding and export complex assembly by HIV Rev. Nat Struct Mol Biol. 2010; 17(11):1337-42.
9. DiMattia M A, Watts N R, Stahl S J, Rader C, Wingfield P T, Stuart D I, et al. Implications of the HIV-1 Rev dimer structure at 3.2 A resolution for multimeric binding to the Rev response element. Proc Natl Acad Sci USA. 2010; 107(13):5810-4.
10. Daugherty M D, D'Orso I, Frankel A D. A solution to limited genomic capacity: using adaptable binding surfaces to assemble the functional HIV Rev oligomer on RNA. Mol Cell. 2008; 31(6):824-34.
11. Groom H C, Anderson E C, Lever A M. Rev: beyond nuclear export. J Gen Virol. 2009; 90(Pt 6):1303-18.
12. Blissenbach M, Grewe B, Hoffmann B, Brandt S, Uberla K. Nuclear RNA export and packaging functions of HIV-1 Rev revisited. J Virol. 2010; 84(13):6598-604.
13. Levin A, Hayouka Z, Friedler A, Loyter A. Nucleocytoplasmic shuttling of HIV-1 integrase is controlled by the viral Rev protein. Nucleus. 2010; 1(2):190-201.
14. Thomas J R, Hergenrother P J. Targeting RNA with small molecules. Chem Rev. 2008; 108(4):1171-224.
15. Yin H, Lee G I, Park H S, Payne G A, Rodriguez J M, Sebti S M, et al. Terphenyl-based helical mimetics that disrupt the p53/HDM2 interaction. Angewandte Chemie-International Edition. 2005; 44(18):2704-7.
16. Suzuki A. Carbon-carbon bonding made easy. Chem Commun. 2005(38):4759-63.
17. Leadbeater N. Fast, easy, clean chemistry by using water as a solvent and microwave heating: the Suzuki coupling as an illustration. Chem Commun. 2005(23):2881-902.
18. Nicolaou K C, Bulger P G, Sarlah D. Palladium-Catalyzed Cross-Coupling Reactions in Total Synthesis. Angew Chem Int Ed Engl. 2005; 44(29):4442-89.
19. Tanious F A, Nguyen B, Wilson W D. Biosensor-surface plasmon resonance methods for quantitative analysis of biomolecular interactions. Methods Cell Biol. 2008; 84:53-77.
20. Dingwall C, Ernberg I, Gait M J, Green S M, Heaphy S, Karn J, et al. HIV-1 tat protein stimulates transcription by binding to a U-rich bulge in the stem of the TAR RNA structure. EMBO J. 1990; 9(12):4145-53.
21. Kjems J, Calnan B J, Frankel A D, Sharp P A. Specific binding of a basic peptide from HIV-1 Rev. EMBO J. 1992; 11(3):1119-29.
22. Tan R, Chen L, Buettner J A, Hudson D, Frankel A D. RNA recognition by an isolated alpha helix. Cell. 1993; 73(5):1031-40.
23. Lacourciere K A, Stivers J T, Marino J P. Mechanism of neomycin and Rev peptide binding to the Rev responsive element of HIV-1 as determined by fluorescence and NMR spectroscopy. Biochemistry. 2000; 39(19):5630-41.
24. Hendrix M, Priestley E S, Joyce G F, Wong C H. Direct observation of aminoglycoside-RNA interactions by surface plasmon resonance. J Am Chem Soc. 1997; 119(16): 3641-8.
25. Peterson R D, Feigon J. Structural Change in Rev Responsive Element RNA of HIV-1 on Binding Rev Peptide. J Mol Biol. 1996; 264:863-77.
26. Hazan U, Thomas D, Alcami J, Bachelerie F, Israel N, Yssel H, et al. Stimulation of a human T-cell clone with anti-CD3 or tumor necrosis factor induces NF-kappa B translocation but not human immunodeficiency virus 1 enhancer-dependent transcription. Proc Natl Acad Sci USA. 1990; 87(20):7861-5.
27. Bauer A W, Kirby W M, Sherris J C, Turck M. Antibiotic susceptibility testing by a standardized single disk method. Am J Clin Pathol. 1966; 45(4):493-6.
28. Halgren T A. Merck molecular force field. 1. Basis, form, scope, parameterization, and performance of MMFF94. Journal of Computational Chemistry. 1996; 17(5-6):490-519.
29. Moustakas D T, Lang P T, Pegg S, Pettersen E, Kuntz I D, Brooijmans N, et al. Development and validation of a modular, extensible docking program: DOCK 5. Journal of Computer-Aided Molecular Design. 2006; 20(10-11): 601-19.
30. Morris G M, Goodsell D S, Halliday R S, Huey R, Hart W E, Belew R K, et al. Automated Docking using a Lamarckian Genetic Algorithm and an Empirical Binding Free Energy Function. J Comp Chem. 1998; 19:1639-62.
31. Verdonk M L, Cole J C, Hartshorn M J, Murray C W, Taylor R D. Improved protein-ligand docking using GOLD. Proteins. 2003; 52(4):609-23.
32. Nguyen B, Tanious F A, Wilson W D. Biosensor-surface plasmon resonance: quantitative analysis of small molecule-nucleic acid interactions. Methods. 2007; 42(2): 150-61.
33. Myszka D G. Improving biosensor analysis. J Mol Recognit. 1999; 12(5):279-84.
34. Goddard T D, Kneller D G. Sparky 3.110. University of California, San Francisco, USA. 2004.
35. Luedtke N W, Tor Y. Fluorescence-based methods for evaluating the RNA affinity and specificity of HIV-1 Rev-RRE inhibitors. Biopolymers. 2003; 70(1):103-19.
36. Adachi A, Gendelman H E, Koenig S, Folks T, Willey R, Rabson A, et al. Production of acquired immunodeficiency syndrome-associated retrovirus in human and non-human cells transfected with an infectious molecular clone. J Virol. 1986; 59(2):284-91.
37. Garcia-Perez J, Sanchez-Palomino S, Perez-Olmeda M, Fernandez B, Alcami J. A new strategy based on recombinant viruses as a tool for assessing drug susceptibility of human immunodeficiency virus type 1. J Med Virol. 2007; 79(2):127-37.
38. Boyle V J, Fancher M E, Ross R W. Rapid, modified Kirby-Bauer susceptibility test with single, high-concentration antimicrobial disks. Antimicrob Agents Chemother. 1973; 3(3):418-24.

The invention claimed is:

1. A compound of formula (I)

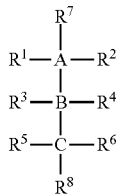 (I)

or a pharmaceutical salt, ester, solvate, or hydrate thereof wherein

A, B and C are benzene, $R^1$ and $R^2$ are in bilateral 1,3 disubstitution relative to each other in benzene A and meta in relation to the carbon atom of A attached to benzene B; and are independently selected from alkyl amine and alkyl guanidine;

$R^3$ and $R^4$ are in bilateral 1,3 disubstitution relative to each other in benzene B and ortho in relation to the carbon atom of B attached to benzene A; and are independently selected from hydrogen, (C1-C6) alkylamide, (C1-C6) alkyl ester, (C1-C6) hydroxyalkyl, (C1-C6) haloalkyl, (C1-C6) alkoxyalkyl, (C1-C8) alkyl, provided that at least one of $R^3$ and $R^4$ is not hydrogen;

$R^5$ and $R^6$ are in bilateral 1,3 disubstitution relative to each other in benzene C and ortho in relation to the carbon atom of C attached to benzene B; and are independently selected from alkyl amine and alkyl guanidine;

$R^7$ and $R^8$ are independently selected from hydrogen, halogen, hydroxyl, (C1-C10) alkoxy, (C1-C10) alkyl amine, (C1-C10) alkyl guanidine, (C1-C10) alkyl amide, (C1-C10) alkylester, (C1-C10) hydroxyalkyl, (C1-C10) alkoxyalkyl, (C1-C10) haloalkyl, (C1-C10) alkyl, aryl alkoxy and aryl ester.

2. A compound according to claim 1 selected from 2",3,5,6"-tetrakis(2-aminoethyl)-4"-methoxy-2',6'-dimethyl-[1,1':4',1"-terphenyl]-4-ol 2,2¹,2",2'-(4"-(benzyloxy)-4-methoxy-3',5'-dimethyl-0 ,1':4',1"-terphenyl]-2,3",5",6-tetray)ptetraethanamine 2",3,5,6"-tetrakis(2-aminoethyl)-Z-ethyl-4"-methoxy-[1,1':4',1"-terphenyl]-4-ol 2,2',2",2-(4'1-(benzyloxy)-3'-ethyl-4-methoxyq1 ,1":4',1"-terphenyl1-2,3",5",6-tetrayl)tetraethanamine 2",3,5,6"-tetrakis(2-aminoethyl)-2',6'-diethyl-4"-methoxy41,1':4',1"-terphenyl1-4-ol 2,2'.2",2"-(4"-(benzyloxy)-3',5'-diethyl-4-methoxy41,1':4',1"-terphenyl1-2,3",5",6-tetrayptetraethanamine or a pharmaceutical salt, ester, solvate, or hydrate thereof.

3. A mihod for the treatment and/or prevention of HIV-1 infections, said method comprising administering a therapeutically effective amount of at least one compound of formula (l) according to claim 1.

4. A pharmaceutical composition comprising at least one compound of formula (I) according to claim 1 or a pharmaceutically acceptable salt, ester, solvate isomer, hydrate or prodrug thereof and a pharmaceutically acceptable excipient.

5. A method for the prevention and/or treatment of HIV-1 infection, said method comprising administering a pharmaceutical composition as defined in claim 4.

6. A pharmaceutical composition according to claim 4 formulated for parenteral, oral, topical, nasal, vaginal or rectal delivery.

7. Method for the preparation of the compounds of formula (I) as defined in claim 1, comprising sequential C-C bond formation via the palladium-catalysed Suzuki coupling of halides, aryltriflates and boronic esters of the bilaterally substituted A, B and C rings where $R^1$, $R^2$, $R^5$, and $R^6$ of the final molecule of formula (I) are introduced by the halide derivatives of A and C and $R^3$ and $R^4$ are introduced by the boronic ester of B.

8. The method according to claim 5, wherein the pharmaceutical composition is formulated for parenteral, oral, topical, nasal, vaginal or rectal delivery.

* * * * *